(12) United States Patent
De Los Santos et al.

(10) Patent No.: US 11,793,870 B2
(45) Date of Patent: Oct. 24, 2023

(54) LIVE ATTENUATED STRAINS OF FOOT AND MOUTH DISEASE MODIFIED BY DEOPTIMIZATION AND USES THEREOF

(71) Applicants: The United States of America, as represented by the Secretary of Agriculture, Washington, DC (US); CODAGENIX INC., Farmingdale, NY (US)

(72) Inventors: Teresa B. De Los Santos, Miller Place, NY (US); Aida E. Rieder, Westbrook, CT (US); Fayna C. Diaz-San Segundo, Blue Point, NY (US); Anna Kloc, Guilford, CT (US); John R. Coleman, Blauvelt, NY (US); Steffen Mueller, Kings Point, NY (US); Gisselle N. Medina, Sound Beach, NY (US)

(73) Assignees: The United States of America, as represented by The Secretary of Agriculture, Washington, DC (US); Codagenix Inc., Farmingdale, NY (US)

( * ) Notice: Subject to any disclaimer, the term of this patent is extended or adjusted under 35 U.S.C. 154(b) by 223 days.

(21) Appl. No.: 17/330,545

(22) Filed: May 26, 2021

(65) Prior Publication Data

US 2021/0401967 A1   Dec. 30, 2021

Related U.S. Application Data

(60) Provisional application No. 63/030,431, filed on May 27, 2020.

(51) Int. Cl.
*A61K 39/135* (2006.01)
*C12N 7/00* (2006.01)
*A61K 39/00* (2006.01)

(52) U.S. Cl.
CPC ............. *A61K 39/135* (2013.01); *C12N 7/00* (2013.01); *A61K 2039/5254* (2013.01);
(Continued)

(58) Field of Classification Search
None
See application file for complete search history.

(56) References Cited

U.S. PATENT DOCUMENTS 8,846,051 B2 * 9/2014 Kew .................. A61K 39/0258
424/229.1
9,476,032 B2 * 10/2016 Wimmer ................. A61P 31/14
(Continued)

FOREIGN PATENT DOCUMENTS

| WO | 2012003129 A2 | 1/2012 |
| WO | 2016115456 A1 | 7/2016 |
| WO | 2018048652 A1 | 3/2018 |

OTHER PUBLICATIONS

Segundo et al. (Journal of Virology. 2016; 90 (3): 1298-1310).*
(Continued)

*Primary Examiner* — Shanon A. Foley
(74) *Attorney, Agent, or Firm* — John D. Fado; Mark D. McNemar

(57) ABSTRACT

The present disclosure describes deoptimized foot and mouth viruses and their use for prophylactic and therapeutic treatment of mammalian subjects. The recombinant viruses provided herein include alterations in several genomic regions as well as Differentiating Infected from Vaccinated Animals (DIVA) markers.

32 Claims, 25 Drawing Sheets
Specification includes a Sequence Listing.

pA$_{24}$Cru-*NheI* (WT)

FseI   NheI   MfeI   BamHI
L   P1   2A   2B   2C   3A   3Bs   3C   3D
1   1616   3912   5423   7487   8191

(52) U.S. Cl.
CPC ............... *A61K 2039/552* (2013.01); *C12N 2770/32121* (2013.01); *C12N 2770/32134* (2013.01)

(56) References Cited

U.S. PATENT DOCUMENTS

2011/0236416 A1    9/2011   Audonnet et al.
2018/0326038 A1   11/2018   Lawrence et al.

OTHER PUBLICATIONS

Segundo et al. (Frontiers in Microbiology. 2021; 11).*
Spinard et al. (Viruses. 2023; 15: 670).*
International Search Report dated May 26, 2021 for PCT/US2021/034282.

* cited by examiner

FIG. 1A  A24P2 (1,517 bp *NheI-MfeI* fragment)  SEQ ID NO: 1

FIG. 1B  A24P3-3B3D (2,001 bp *MfeI-BamHI* fragment)  SEQ ID NO: 2

FIG. 1C  A24P2/P3-3B3D (3,512 bp *NheI-BamHI* fragment)  SEQ ID NO: 3

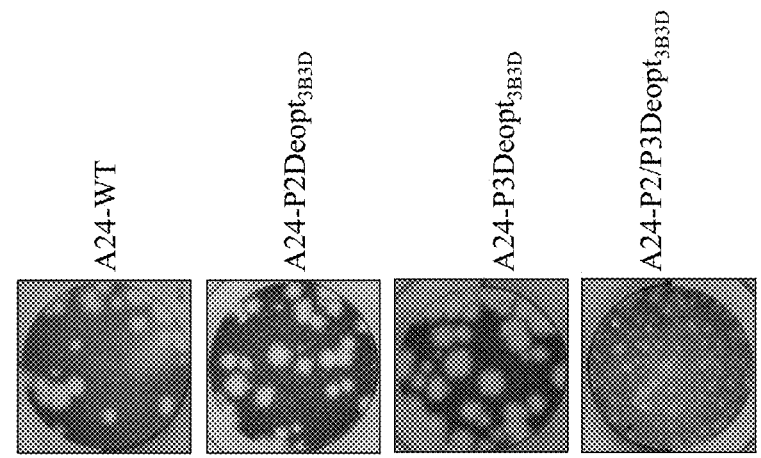
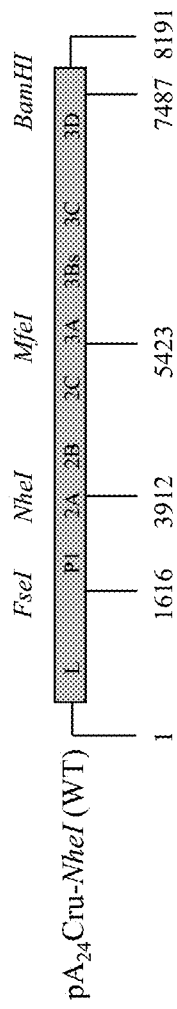
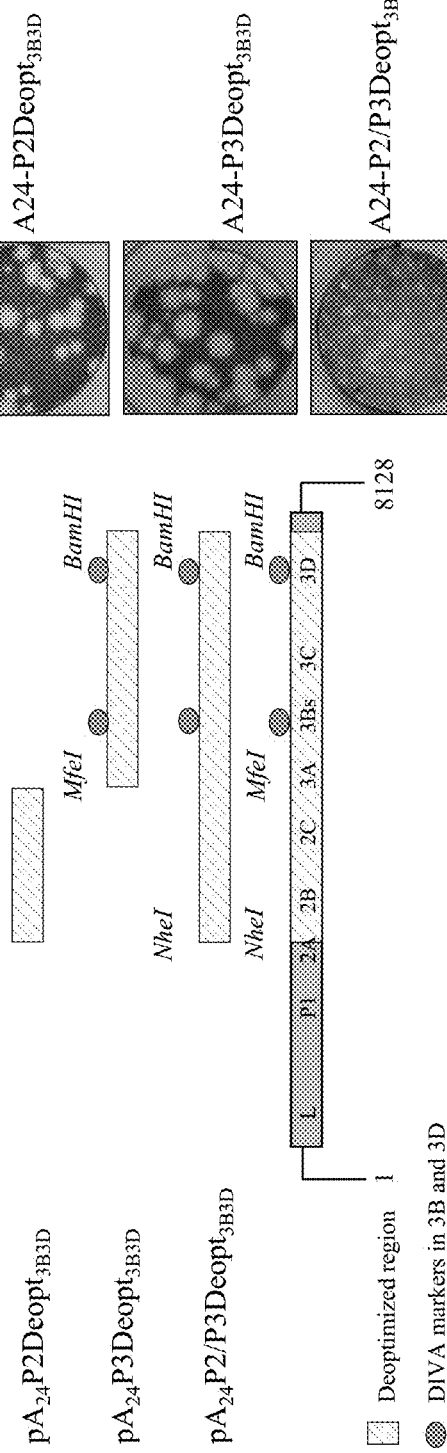
FIG. 2A
FIG. 2B
FIG. 2C

A₂₄P1-Deopt₃ᵦ₃ᴅ (2,218 bp FseI-NheI fragment) (SEQ ID NO: 4)

GGGGCCCGGCCAATCGAGTCCCGCTACCGGTTCGCAAAACCAATCCGGTAACACCGGATCGATCATTAACAATTACTATATGCAGCA
ATACCAGAACTCTATGGACACACAGTTGGGCGACAACGCTATCTCCGGCGATCGAACGAGGGGTCAACCGACACTACGAGTACGC
ATACGACTAACACACAGAATAACGATTGGTTTCGAGGACTCGCTTCATCCGCTTCATCCGCTTGTTCGGCGCACTGCTTGCCGAT
AAGAAGACCGAAGAGACTACGTTGCTCGAGGACCGGATTCTGACTACGCGGTAACGGTCACACAACATCGACAACATCGACAATCGTCAGT
CGGCCGTGACACGACACGGGTACTCAACCGAAGAGGAACCACGTTCGCCGGACCAAAAGCGTTCGGTCACCTCGAGAAACTCGAGTTGTGCAGGCCG
AACGGTTTTACAAAAAGTATCTGTTCGATTGGACTACGCTTACATGCTTCGGTCACCATGCTTACATGGGTCGAGGGTGGGACACGTCGAGGTGTCCGCGTAGGCAATCAGTT
CACGGGCGTGTTCGGCACCTTGGTCGCGATGGTGCCCGATGGTGCCCGAATGGAAAGAGTTCGACACGCGAAACTTGGCGTTAACAGATACGACCAATACAAAAAG
ACCAATTCATTAGTCCGCGAACGAACATGACCGCTCACATTACCGTGCCATACCTTGGCGTTAACACTAGTGCGCACAGATTAAGTGTACGCTAA
CACAAGCCTTGGACACTCGTTGTGATGGTCCGCCGGCAATTGCCGTCTAAGGAGGGGATCTTCCCGTCGCATGGCGCCGACGGATACGGCG
CATCGCACCGACATACGTGCACGTCGACCCTAAGACCGCCGGACGCCGTGTCCGAAGCGTGTGCCGAAGCCTAAGGTGTACAATCGCCTAGACCGGTAAGCCATAGCGGTAACTACCCCCGGTAGGTTT
GACTCGTGACTACCGACCCTAAGACCGCCGGACGCCGTGTCCGAAGCGTGTGCCGAAGCCTAAGACCGGTAAGCCATAGCGGTAACTACCCCCGGTAGGTTT
ACGAACTTGCTCGACGTCGCCGAAGCGTGTTCGACCTGTCACTCGCCTAAGCATATGTCTAACACATACCTATCCGGTATCGCGCAATACTATA
CACTAGACTGCTTGCGAAATTCGACCTGTTGCACTTATGTTACCGGATCGACCGACTCTAAGGCTAGGTATATGGTCGCATACATTCCG
CGCAATACTACCCGGTACGATTAACTTGCACACCCCGACACGCGCCGAATGGACACACCGGGCTTAACTCTAAGTT
CCTGGCGTCGAGACACCCCCGACACGCGCCGAATGGACACTGTATCCACGCCGAATGGACACACCGGGCTTAACTCTAAGTT
TACGTTTTCGATCCCATACGTGTCCGCCGGATTACGGCATACACGACACACTCGTAGTGTCGCCGGTTAGCGCCGGTAAGGACTTCGAGTTGCGG
TGTGCATATACCAGATTACGCACGTTAGGCCGTAAGGCCGTAAAACGACACACTCGTAGTGTCGCCGGTTAGCGCCGGTAAGGACTTCGAGTTGCGG
TTGCCGATCGACCCTAGACAGACACCATACCGCTACCGCTACCCGGACGGCTACCGACACGGAACTCGTCGTCGCTACGGCAGTCGAGAATTACGGCGGTGA
GACACAGATCCAACGGAGACACCATACCGCTACCGCTACCCGGACGGCTACCGACACGGAACTCGTCGTCGCTACGGCAGTCGAGAATTACGGCGGTGA
TGATCGACCTTATGCAGACGAGGGTAACCTGCACATGGGTGCCTAAGCGGACTCGTTGCGCGCCGTACATACTACTTTTCCGACCTCGAGATC
GTCGTGCGACACGAGGGTAACCTGCACATGGGTGCCTAAGCGGACTCGTTGCGCGCCGTACATACTACTTTTCCGACCTCGAGATC
CAACAAAGCGCCATTCACACGACTCGACGCGGGACATGGGTCACTCGCCGTATGAAACGCGCCGAACTGTATTGCCCTAGACCGTACGTCTAAGT
ACGCCGTAGGCGGTCCGGTAGACGCGGGACATGGGTCACTCGCCGTATGAAACGCGCCGAACTGTATTGCCCTAGACCGTACGTCTAAGT
GGCGCAATCAAGGCCGACTCGACGCGGGACATGGGTCACTCGCCGTATGAAACGCGCCGAACTGTATTGCCCTAGACCGTACGTCTAAGT
CGAGGTGAGTTCGCAAGACAGACAGAACAAACAGAAGATTATCGCCCCGCTAAGCAGCTTCTGAATTTTGACCTGCTCAAGCTAGC

FIG. 13

ASIA-P1Deopt$_{3B3D}$ (2,218 bp FseI-NheI fragment) (SEQ ID NO: 5)

```
GGGGCCGGCCAATCTAGTCCCGCTACCGGTAGTCAGAACCAGTCCGTAACACCGATCGATCATTAACAACTACTATATGCAGC
AATACCAGAACTCTATGGACACACAGTTGGGCGATAACGCTATCTCAGGCGATCGAACGAGGGGTCGACGACTACCTCTAC
GCACACTAACACACACAGAATAACGACTGGTTTTCGCGACTTGCTCGAGGATCGCATACGACTGCTCTAGCGCGTTAGCGCCACTGCTTGCC
GATAAGAAGAGACGAAGAGACTACGTTGCTCGAGGATCGCATACTGACTTAGCGGACCGGTAACGGTCACACTACGAGTACGACACAGTCTA
GCGTAGGCGTGACATACGGATACGCCGTTGCGGAGGACGCCGTTAGCGGACCGACTAGCGACTCGAGACTCGAGAGCGTACAGCA
GGCCGAACGGTTCTTTAAGAAACACCTATTCGATTGGACCTCGAACCTCGAACACATGCGTAACGGGTGGGACATCGAGGTGACCGAGTCGGTA
GAACACAAAGGCGTGTACGGATCGCTTATGGGGTCATACGCATACATACGCGTAACGGGTGGGACATCGAGGTGACCGAGTCGGTA
ACCAGTTTAACGGGGGGTGTCTGTTAGTCGCGCTTGTGCCCGGAACTGAAAGAGCTTGACACACGCCAAAAGTACCAACTGACACT
GTTCCCACACCAATTCATTAACCCTAGGACACTCGTCGTCGAGGACTCGTCGTCGCGGCGAGTTGCCGTGCCCGTCGCCGGCGGTCCGAACAGATTAAGG
TACGCTCTGCACAAGCCTTGGACACTCGTCGTCGAGGACTCGTCGTCGCGGCGAGTTGCCGTGCCCGTCGCCGGCGGTCCGAACAGATTAAGG
TGTATATGAACGCTGCGCCAACATACGTGCACGTTGCCGGCGAGTTGCCGCGGGATCGTCGCCCGTCGCCATGCCGCGA
CGGATACGGTAACATGGTGACTACCGACCCTAAGACCCGGCGAAGCGTGCCCTACATTCCTTAGGTTCGGCGAAGTGCCATTCGTTAAGACCG
CCCGGTAGGTTACGGAACTTTCTGACGTCGCCGAAGCGTGCCCTACATTCCTTAGGTTCGGCGAAGTGCCATTCGTTAAGACCG
TGAACTCCGGCGATCGCTTGCTCGCGAAATTCGACGTGTCACTCGCGGTCACATGTCTAACACATACCTTGCCGACTCGC
GCAATACTATACGCAATACTCCGGTACGATGAACGTGCACTTTATGTTTACCGGACCCGACCGACCGCTAAGGCTAGGTATATGGTC
GCGTACGTTCCCCCGGTATGACACCCCATACCGACCCCGAACACGCCGACTACGCTTACACCGGAGCGACGTTGCCGAAACGACTAGCGT
ACTCTAAGTTTACGTTTTGCGATCCCATACCGACCCCGAACACGCCGACTACGCTTACACCGGAGCGACGTTGCCGAAACGACTAGCGT
GCAGGGGTGGGTGTGTATCTACCAGATTACGCACGCTAAGGCCACGGCTAAGGCCGAGAATCCGCCAGTCCGTTACGACTACCGTCGAGA
TTCGAGTTTCGCTTGCCCGTTGACGCTAGGCAGCAGATGCACTGCATACCGACGTTGCGTTCATACTCGACCGGTTCGTTAAGCTTACCGGCCC
ACTACGGCGGAGAGACACAGACCGCTAGGCGACTGCATACCGACGTTGCGTTCATACTCGACCGGTTCGTTAAGCTTACCGGCCC
TAAGAATATCCAGACACTCGACCTTATGCAGATCCCGTCACACACACTCGTAGGCGCACTGTTGCGCTCTGCGACATACTACTTT
TCCGACCTCGAGGTCGCGCTTGTGCACACCGGTCCCGTGACATGGGTGCCTAACGGCGCACTGCCGAAAGACGCACTGAACAACCAGA
CTAACCCTACCGCATACCAGAAACGCCCTATTACGGCGACTACCTCTAGGCGCGACGCATGCCGCAACGCCCACTCGCGCAACGCCCTATCCGCTAGACTGCCA
TAACGGTAAGACCGCATACGGCGAGACTGCCGTTAAGGCGAGACTGCCCTATAGGCCGCAACGCCCACTCGCGCAACGCCCTATCCGCTAGACTGCCA
ACGTCATTCAATTACGCGCCACTCGATACGCGAGACTGTTATCCGTATGAAAACGCGCTGAGACATATGTCCAC
GCCCCCTACTCGCTCGACTCGATACGCGAGACTCAGGACAGAGACGCAAACAGGAGATAATCGCACCCGAGAAACAGCTTCTGAATTTTGACCT
GCTTAAGCTAGC
```

FIG. 14

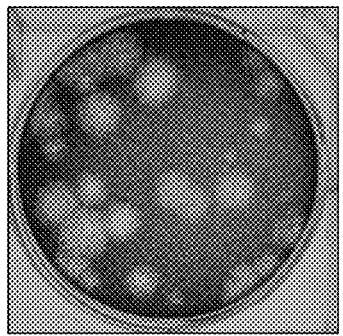
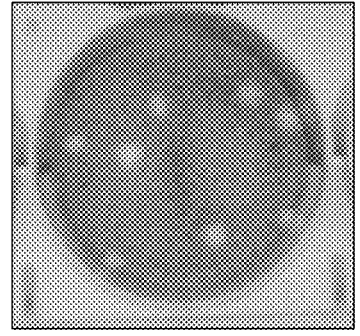
FIG. 15A
FIG. 15B

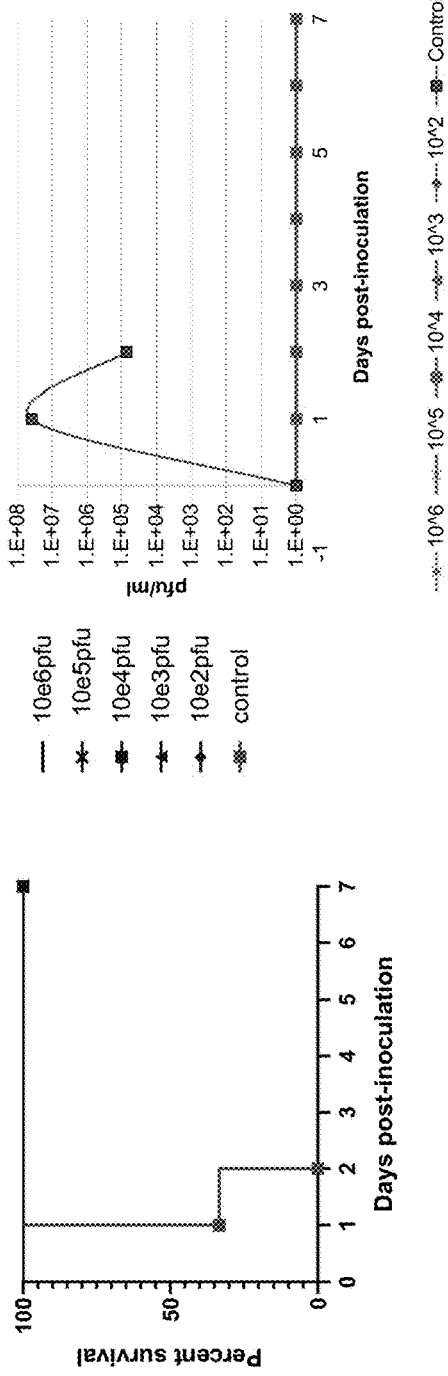
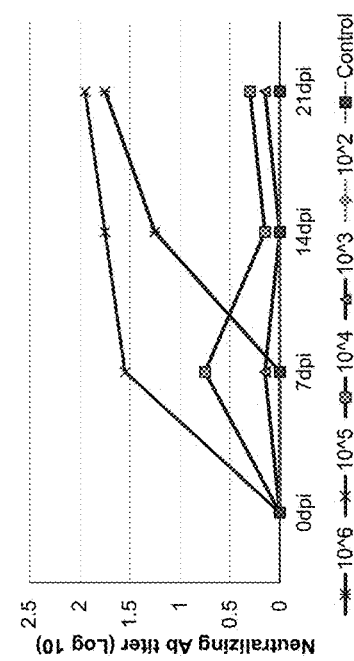
FIG. 22A
FIG. 22B
FIG. 22C

LIVE ATTENUATED STRAINS OF FOOT AND MOUTH DISEASE MODIFIED BY DEOPTIMIZATION AND USES THEREOF

CROSS-REFERENCE

The present application claims priority to U.S. Provisional Patent Application Ser. No. 63/030,431 filed on May 27, 2020 the content of which is expressly incorporated herein by reference.

BACKGROUND OF THE INVENTION

Field of Invention

This invention relates to attenuated viruses and the prophylactic and therapeutic treatment of viral disease.

Background

Foot-and-mouth disease (FMD) is one of the most highly contagious viral diseases of cloven-hoofed animals and it is caused by the FMD virus (FMDV), a member of the Picornaviridae family. The virus can infect over 70 species of livestock and wild animals including cattle, swine, sheep, goat, and deer. FMD is listed by the International Organization of Animal Health (OIE) as a reportable disease and severe trading restrictions are imposed upon notification of an outbreak. Disease outbreaks in previously FMD-free countries are initially controlled by culling of infected and in-contact animals, restriction of susceptible animal movement, disinfection of infected premises and occasionally, vaccination with an inactivated whole virus antigen preparation. In countries where the disease is enzootic animals are prophylactically vaccinated. While not hazardous to human health, an FMD outbreak carries severe economic costs. For instance, the recent UK outbreak of 2001, afforded economic losses that surpassed US$12 billion, seriously impacting the overall economy of the affected areas.

In addition to the inactivated whole antigen vaccine formulation, a recombinant vaccine involving a replication defective human adenovirus 5 that delivers empty FMDV capsids (Ad5-FMD) has been successfully tested in recent years, however thus far this vaccine has only been granted a conditional license in the U.S. and its production could be costly. Both, the inactivated vaccine and the Ad5-FMD vaccine, require approximately 7 days to induce protective immunity in swine and cattle and the duration of immunity is shorter than that conferred by natural infection. As a result, vaccinated animals are susceptible to disease if exposed to FMDV prior to 7 days or after approximately 6 months post vaccination.

The Global Foot-and-Mouth Disease Research Alliance (GFRA), an international organization launched in 2003, has set as part of their five main goals, the development of next generation control measures and strategies including improved vaccines and biotherapeutics.

It has been reported that rapid and long-lasting protection against viral infection is usually best achieved by vaccination with live attenuated vaccines (LAVs). Indeed, using attenuated viral vaccines, smallpox and rinderpest viruses have been eradicated and measles has been eliminated from some parts of the world. Due to full or partial virulence in animals or reversion to virulence of experimental modified attenuated FMDV candidates, no LAV has been successfully developed or implemented to control FMDV. Previously described efforts examining genetically engineered leaderless FMDV strains, carrying a deletion of the nonstructural viral protein $L^{pro}$ coding region, showed reduced pathogenicity in swine and cattle. However, animals inoculated with a leaderless virus were not completely protected when challenged with certain wild type (WT) viruses. More recently, a highly attenuated marker leaderless FMDV termed "FMDLL3B3D" (Uddowla et al, J. Virol. (2012) 86:11675-11685) was developed showing no signs of disease in the natural host, when administered live. In fact, the additional modifications including negative antigenic (3B and 3D) marker introduced in the FMDLL3B3D backbone, and a deletion of one of three 3B copies in the viral genome, rendered this mutant virus very stable and further restricted its replication in cattle or swine (Uddowla et al, supra; Eschbaumer et al, Pathogens, (2020) 9:129). The attenuation of this novel vaccine candidate is such that the FMD-LL3B3D $A_{24}$ Cruzeiro vaccine platform strain and a large number of capsid coding cassettes were excluded from the United States Select Agent Program regulations in April 2018 (Select Agent Program. (2020). Foot and Mouth Disease. www.selectagents.gov/exclusions-usda.html#footmouth) and that currently, it has been license in the US for manufacturing as a chemically inactivated safe FMDV marker vaccine (not as an LAV). This vaccine platform encodes two unique restriction sites to flank the capsid coding region to accommodate swapping capsid coding cassettes. Other experimental LAV vaccines carrying $L^{pro}$ mutations introduced in a conserved protein motif, SAF-AB, Acinus and PIAS (SAP) domain (de los Santos et al, J. Virol., (2009) 83:1800-1810), have also been described. Specifically, substitutions of two conserved amino acid residues in this domain in FMDV A12 generated an attenuated mutant virus in cell culture and in swine. Interestingly, when the modified attenuated strain was tested as a vaccine candidate in swine, animals were completely protected even when challenged as early as two days post vaccination. However, since only two amino acid residues were substituted, reversion to virulence of the SAP mutant poses a considerable risk.

Codon usage bias is characteristic of all biological systems since the frequencies of synonymous codon use for each amino acid are unequal. Despite the low codon usage bias in RNA viruses deoptimization of the P1/capsid region has proven to be an effective genetic engineering technique to attenuate poliovirus, which like FMDV belongs to the Picornaviridae family of viruses. Independently of the "codon bias" concept, some synonymous codon pairs are used more or less frequently than statistically predicted, resulting in a particular "codon pair bias" in every examined species.

SUMMARY OF THE INVENTION

The following embodiments and aspects thereof are described and illustrated in conjunction with compositions and methods which are meant to be exemplary and illustrative, not limiting in scope.

The present disclosure provides, in one embodiment, a deoptimized foot and mouth disease virus (FMDV) containing a substituted genomic region, where the substituted genomic region is a nucleic acid at least 95% identical to SEQ ID NO: 1, SEQ ID NO: 2, SEQ ID NO: 3, SEQ ID NO: 4, SEQ ID NO: 5, SEQ ID NO: 6, or SEQ ID NO: 7, and encodes the same polypeptide as SEQ ID NO: 1, SEQ ID NO: 2, SEQ ID NO: 3, SEQ ID NO: 4, SEQ ID NO: 5, SEQ ID NO: 6, or SEQ ID NO: 7, respectively, or encodes the same polypeptide as SEQ ID NO: 1, SEQ ID NO: 2, SEQ ID NO: 3, SEQ ID NO: 4, SEQ ID NO: 5, SEQ ID NO: 6, or SEQ ID NO: 7, respectively, with up to 10 amino acid replacements, deletions or additions. In some embodiments, the deoptimized FMDV has a substituted genomic region comprising a nucleic acid at least 99% identical to, or 100% identical to, SEQ ID NO: 1, SEQ ID NO: 2, SEQ ID NO: 3, SEQ ID NO: 4, SEQ ID NO: 5, SEQ ID NO: 6, or SEQ ID NO: 7. In some embodiments, deoptimized FMDV also contain a DIVA marker, such as mutations in the 3B and 3D coding regions.

The present disclosure further provides, in an additional embodiment, a deoptimized modified foot and mouth disease virus (FMDV) constructed by substituting the P2 domain, or the P3 domain with a codon deoptimized or codon-pair deoptimized region encoding the same protein sequence, or encoding a protein sequence with up to 10 amino acid replacements, deletions or additions, where the codon pair bias of the modified sequence is less than the codon pair bias of the parent FMDV, and is reduced by 0.05, 0.1, or 0.2. In particular embodiments, the deoptimized genomic region is the P2 domain, the P3 domain, or both the P2 and P3 domain. In specific embodiments, the deoptimized FMDV is A24-P2-3B3D, A24-P3-3B3D, or A24-P2/P3-3B3D.

The present disclosure further provides process embodiments, including a method of eliciting an immune response to foot and mouth disease, by administering any of the deoptimized modified viruses described herein to a mammalian subject. In some embodiments, administering the deoptimized modified virus is done by administering $10^2$, $10^3$, $10^4$ or $10^5$ pfu/mammalian subject of the deoptimized modified virus. In some embodiments, the subject is a bovid or a suid. In additional embodiments, administering the deoptimized modified virus entails administering a prime dose, and one or more boost doses, to the mammalian subject. In some embodiments of this method, the prime dose is administered when the mammalian subject does not have foot and mouth disease. In some embodiments of this method, the one or more boost doses are administered when the mammalian subject does not have foot and mouth disease. In some embodiments of this method, the one or more boost doses are administered when the mammalian subject has been exposed to foot and mouth disease. In some embodiments, the immune response elicited by this methodology is a protective immune response.

Other features and advantages of the invention will become apparent from the following detailed description, taken in conjunction with the accompanying drawings, which illustrate, by way of example, various features of embodiments of the invention.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE FIGURES

The novel features of the invention are set forth with particularity in the claims. Features and advantages of the present invention are referred to in the following detailed description, and the accompanying drawings of which:

FIG. 1A, FIG. 1B and FIG. 1C depict sequences of A24Cru with deoptimized P2 and/or P3 and 3B3D DIVA markers. FIG. 1A depicts SEQ ID NO: 1. FIG. 1B depicts SEQ ID NO: 2. FIG. 1C depicts SEQ ID NO: 3.

FIG. 2A, FIG. 2B and FIG. 2C depict the generation of deoptimized FMDV. FIG. 2A: Schematics of $A_{24}$Cru wild type (WT) infectious clone (Rieder et al 2005) with a unique added NheI site. Relevant restriction sites used for cloning are depicted (NheI, MfeI and BamHI). (FIG. 2B) NheI/MfeI, MfeI/BamHI of NheI/BamHI fragments containing deoptimized codons (Burns et al., 2006) were synthesized and respectively replaced in $pA_{24}$CruNheI. Synthesized fragments contained DIVA markers including a small deletion in 3B and amino acid substitutions in 3B and 3D (Uddowla et al. 2012). FIG. 2C: Plaque morphology of WT and deoptimized viruses was analyzed in BHK-21 cells. Plaques were developed at 48 hpi. (see Example 1).

FIG. 3A, FIG. 3B, FIG. 3C, and FIG. 3D depict kinetics of growth and plaque morphology in cell culture. BHK-21 (FIG. 3A) and IBRS2 (FIG. 3B) cells lines or PK (FIG. 3C) and EBK (FIG. 3D) primary cells were infected with FMDV $A_{24}$Cru wild type (A24-WT) or deoptimized variants, A24-P2Deopt$_{3B3D}$, A24-P3Deopt$_{3B3D}$ and A24-P2/3Deopt$_{3B3D}$ at MOI=2. After 1 h incubation, unabsorbed virus was removed by washing with 150 mM NaCl, 20 mM MES (pH=6.0) followed by addition of MEM complete media and incubation at 37° C. Samples were taken at 1, 3, 6 and 24 hpi and virus titers were determined by plaque assay on BHK-21 cells.

FIG. 4A, FIG. 4B and FIG. 4C depicts deoptimized viruses are attenuated in vivo in mice. 6 to 7 weeks old female C57BL/6 mice (n=6/group) were subcutaneously inoculated in the footpad with FMDV A24-deoptimized mutants, A24-P2/P3Deopt, A24-P2Deopt or A24-P3Deopt at the indicated doses (plaque forming units—pfu-/animal). One group was inoculated with $1\times10^5$ pfu/animal of A24-wild type (WT) as control. FIG. 4A: Survival rates determined daily post inoculation. FIG. 4B: Virus titers were measured in serum samples collected for 7 days post inoculation (dpi). FIG. 4C: FMDV specific antibody neutralizing titers were measured in serum samples collected at 0, 5, 7, 14 and 21 dpi with deoptimized variants and after 7- and 14-days post challenge (dpc) in all animals that survived the initial inoculation.

FIG. 9 depicts determination of FMDV neutralizing antibodies in the serum of animals inoculated with A24-P2, P3 or P2/P3Deopt$_{3B3D}$ or A$_{24}$Cru wild type (A24-WT).

FIG. 12 depicts determination of FMDV neutralizing antibodies in the serum of animals inoculated with A24-P2/P3Deopt$_{3B3D}$ or A$_{24}$Cru wild type (A24-WT) Presence of FMDV neutralizing antibodies was evaluated by a microtiter neutralization assay on BHK-21 cells in sera of animals inoculated with different doses of A24-P2/P3Deopt$_{3B3D}$ or WT at the indicated time points after inoculation. Titers are reported as the log$_{10}$ of the reciprocal of the highest dilution of serum that neutralized the virus in 50% of the wells. Each data point represents the mean±standard deviation (SD) of each group.

FIG. 13 depicts sequences of A24Cru with deoptimized P1 region in the A24Cru IC containing 3B3D DIVA markers and denoting restriction sites (FsseI and NheI) used for cloning (SEQ ID NO: 4).

FIG. 14 depicts sequences of Asia1 deoptimized P1. Underlined are FseI and NheI restriction sites (SEQ ID NO: 5).

FIG. 15A and FIG. 15B depict generation of A24-P1 Deopt$_{3B3D}$ virus. (FIG. 15A) Cloning strategy to generate A24-P1 Deopt$_{3B3D}$ infectious clone. (FIG. 15B) Plaque morphology of A24-WT3B3D and A24-P1 Deopt$_{3B3D}$. Plaques were developed at 48 hpi in BHK-21 cells.

(FIG. 16A) Cloning strategy to generate ASIA-P1 Deopt$_{3B3D}$ infectious clone. (FIG. 16B) Plaque morphology of A24-WT3B3D and ASIA-P1 Deopt$_{3B3D}$. Plaques were developed at 48 hpi in BHK-21 cells.

(FIG. 17A) BHK-21 and (FIG. 17B) SK6 cells were infected with the indicated viruses at MOI=5. After 1 h incubation, unabsorbed virus was removed by washing with 150 mM NaCl, 20 mM MES (pH=6.0) followed by addition of MEM complete media and incubation at 37° C. Samples were taken at 1, 2, 4, 7 and 24 hpi and virus titers were determined by plaque assay on BHK-21 cells.

(FIG. 18A) Survival rates were calculated as (number of surviving animals/number of animals per group)×100, daily post inoculation. (FIG. 18B) Virus titers were measured in serum samples collected for 7 days post inoculation (dpi). (FIG. 18C) Presence of FMDV neutralizing antibodies was evaluated by a microtiter neutralization assay on BHK-21 cells in sera of animals inoculated with different doses of A24-P1 Deopt$_{3B3D}$ at the indicated time points after inoculation or challenge. Control animals died due to disease before 7 dpi. Titers are reported as the log 10 of the reciprocal of the highest dilution of serum that neutralized the virus in 50% of the wells. Each data point represents the mean±standard deviation (SD) of each group.

FIG. 22A, FIG. 22B, and FIG. 22C depict deoptimized viruses are attenuated in vivo in mice. 6 to 7 weeks old female C57BL/6 mice (n=6/group) were subcutaneously inoculated in the footpad with FMDV ASIA-P1 Deopt$_{3B3D}$ at the indicated doses (plaque forming units—pfu-/animal) or Asia1 at 4×10$^5$ pfu/animal (control). (FIG. 22A) Survival rates determined daily post inoculation. (FIG. 22A) Virus titers were measured in serum samples collected for 7 days post inoculation (dpi). (FIG. 22A) FMDV specific antibody neutralizing titers were measured in serum samples collected at 0, 5, 7, 14 and 21 dpi with the different viruses and doses FIG. 23 depicts clinical outcome in animals inoculated with ASIA-P1 Deopt$_{3B3D}$ or ASIA-WT. 18-23 kg castrated male Yorkshire swine (n=4/group) were inoculated with 10$^6$ plaque forming units (pfu) [animals 81 to 84], 10$^5$ pfu [animals 85 to 88] or 10$^3$ pfu [animals 89 to 92] of FMDV ASIA-P1 Deopt$_{3B3D}$ or 10$^5$ pfu [animals 93, 95 & 96] of FMDV ASIA-WT. Animals were monitored for 7 days and samples of heparinized blood, serum and nasal swabs were collected every other day. Clinical score (blue bars) and % of lymphocytes (green line) for each animal are represented.

FIG. 25 depicts determination of FMDV neutralizing antibodies in the serum of animals inoculated with ASIA-P1 Deopt$_{3B3D}$ or ASIA-WT. Presence of FMDV neutralizing antibodies was evaluated by a microtiter neutralization assay on BHK-21 cells in sera of animals inoculated with different doses of ASIA-P1 Deopt$_{3B3D}$ at the indicated time points after inoculation. Titers are reported as the log 10 of the reciprocal of the highest dilution of serum that neutralized the virus in 50% of the wells. Each data point represents the mean±standard deviation (SD) of each group.

DETAILED DESCRIPTION OF THE INVENTION

Figure 5:
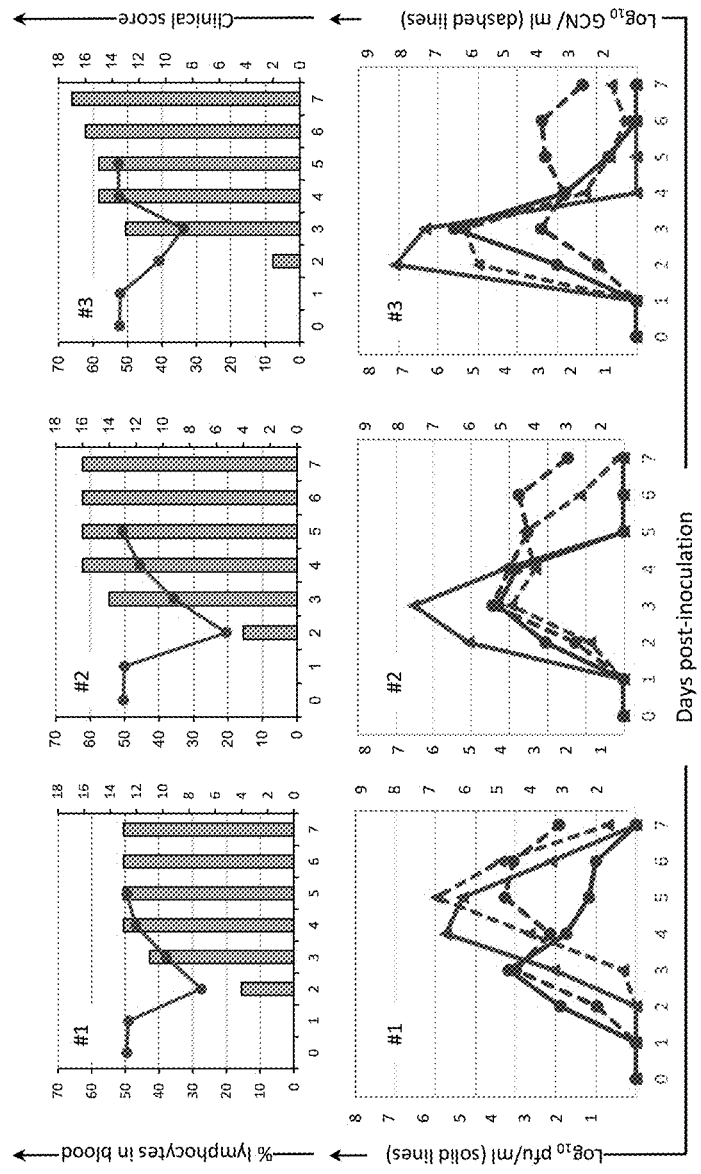
FIG. 5 depicts clinical outcome in animals inoculated with A24-WT. 18-23 kg castrated male Yorkshire swine (n=3/group) were inoculated with $10^5$ plaque forming units (pfu) of FMDV A24-WT. Animals were monitored for 7 days and samples of heparinized blood, serum and nasal swabs were collected daily. Clinical score (blue bars) and % of lymphocytes (green line) for each animal are represented in the top panels; Virus isolation in serum (red line) and nasal secretion (blue line) and presence of viral copy numbers (GCN) per ml of serum (red dashed line) and nasal secretion (blue dashed line) are presented in the bottom panels.

Foot-and-mouth disease (FMD) is one of the most feared viral diseases that can affect livestock. Although this disease appeared to be contained in developed nations, recent outbreaks have demonstrated that infection can spread rapidly, causing devastating economic and social consequences. To develop novel countermeasures, "synonymous codon deoptimization" of certain coding regions of the FMDV genome was performed to produce stable modified attenuated viral strains. Mutant viruses were also engineered to contain specific mutations in the 3B and 3D coding regions that confer markers for differentiation of infected from vaccinated animals (DIVA), and convenient restriction endonuclease cleavage sites for capsid swapping. Deoptimization of selected coding regions, including DIVA markers, resulted in viable progeny that exhibited attenuation in cell culture, in mice and in swine, a natural host. Our work demonstrates that codon deoptimization technologies can be applied to FMDV to obtain modified live attenuated strains of FMDV containing DIVA markers, reduced risk for reversion and recombination with virulent circulating strains for potential development as modified vaccine candidates.

Herein we demonstrate that stable, viable strains of FMDV can be produced by deoptimization of genomic regions other than the capsid regions. Deoptimization of conserved P2/P3 FMDV regions resulted in attenuated strains that can grow to end point titers similar to those of the parental WT strain in tissue culture. Furthermore, P2/P3 deoptimized variants tolerated the introduction of: A) DIVA (differentiation of infected from vaccinated animals) markers in the 3B and 3D regions, and B) restriction sites for easy capsid exchange.

All together, these results demonstrate that codon/codon pair bias deoptimization is applicable to multiple targets as a means to derive viable strains of reduced virulence, and decreased probability of recombination, while allowing for maintenance of genetic markers for differential diagnostics, highlighting their potential for development into modified live attenuated FMDV vaccine candidates.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); March, *Advanced Organic Chemistry Reactions, Mechanisms and Structure* 7$^{th}$ ed., J. Wiley & Sons (New York, N.Y. 2013); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

"Coding sequence" as used herein refers to a nucleic acid sequence encompassing an open reading frame or part thereof, which encodes a viral or host cell protein sequence or part thereof.

Modified sequences (nucleic acids, proteins) of the present invention also include nucleic acids with high identity to a reference sequence. For example, nucleic acids having 80%, 81%, 82%, 83%, 84%, 85%, 86%, 87%, 88%, 89%, 90%, 91%, 92%, 93%, 94%, 95%, 96%, 97%, 98% or 99% identity to any of the sequences provided herein. As a practical matter, percentage identity to a given reference sequence can be determined conventionally using known computer programs to find the best segment of homology between two sequences. When using sequence alignment program(s) to determine whether a particular sequence is, for instance, 96% identical to a reference sequence according to the present invention, the parameters are set, of course, such that the percentage of identity is calculated over the full length of the reference sequence.

The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

"Deoptimized modified viruses" as used herein refer to viruses in which their genome, in whole or in part, has synonymous codons and/or codon rearrangements and variation of codon pair bias. Deoptimized modified viruses of the present invention can be used to for prophylactic and therapeutic treatment of viral infections.

"Mammal" as used herein refers to any member of the class Mammalia, including, without limitation, humans and nonhuman primates such as chimpanzees, and other apes and monkey species; farm animals such as cattle, buffalo, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be including within the scope of this term.

We believe that codon and codon-pair bias deoptimization can also be a useful tool to develop attenuated vaccine candidates against any RNA virus. In various studies we have recently demonstrated that, codon-pair bias deoptimization is also tolerated by FMDV. Deoptimization of the P1 structural region resulted in a FMDV strain (A12-P1 deopt) that was highly attenuated in mice, and that induced a protective immune response against lethal FMDV WT challenge at a relative low dose offering an approximately ~10,000 "safety margin" (ratio between the dose required to kill animals and the dose required to induce protection) (Diaz-San Segundo et al, J. Virol., (2015) 90:1298-1310). Furthermore, virulence studies in swine showed that the A12-P1 deopt virus was also attenuated in the natural host since a dose ~100 fold higher than the dose of homologous WT virus was required to cause equivalent disease. Interestingly, high levels of neutralizing antibodies (Abs) were detected in sera suggesting that swine vaccinated with A12-P1 deopt virus could be protected against FMD.

FMDV structural proteins are involved in capsid assembly and stability, virus binding to target cells, and antigenic specificity, influencing significant aspects of virus infection and immunity. The high level of variability in FMDV capsid proteins reflects selective pressures and virus adaptation, as represented by the multiple serotypes and subtypes of this virus. In contrast, other regions of the viral genome are more conserved and can be substituted for each other in infectious FMDV clones without affecting viability. In fact, we have recently shown that a master seed vaccine strain could be constructed with the $A_{24}$Cru IC backbone and specific capsids could be exchanged without significantly affecting the virus growth properties.

Described herein, we demonstrate that stable viable strains of FMDV can be produced by deoptimization of other than the capsid regions. Deoptimization of conserved P2/P3 regions resulted in attenuated strains that in tissue culture can grow to end point titers similarly to those of the parental WT strain. Furthermore, introduction of DIVA markers in the 3B and 3D regions and restriction sites for easy capsid exchange were well tolerated in the P2/P3 deoptimized variants. Among the different mutants obtained and evaluated, studies in mice and swine demonstrated that the resulting A24-P2/P3Deopt$_{3B3D}$ virus was attenuated in vivo and induced an adaptive immunity. These results highlight the potential of codon deoptimization as a strategy to reduce the virulence of FMDV and decrease the probability of recombination with circulating strains, making them attractive candidates for further development into modified live attenuated FMDV vaccines. Various embodiments of the present invention are based, in part, on these finding, as well as those further described herein.

Alternative Encoding

A given peptide can be encoded by a large number of nucleic acid sequences. For example, even a typical short 10-mer oligopeptide can be encoded by approximately $4^{10}$ (about $10^6$) different nucleic acids, and the P1 capsid protein of poliovirus (881 amino acid long) can be encoded by about $10^{442}$ different nucleic acids. Natural selection has ultimately chosen one of these possible $10^{442}$ nucleic acids as the PV genome. Whereas the primary amino acid sequence is the most important level of information encoded by a given mRNA, there are additional kinds of information within different kinds of RNA sequences. These include RNA structural elements of distinct function (e.g., for PV, the cis-acting replication element, or CRE, translational kinetic signals (pause sites, frame shift sites, etc.), polyadenylation signals, splice signals, enzymatic functions (ribozyme) and, quite likely, other as yet unidentified information and signals).

Even with the caveat that signals such as the CRE must be preserved, $10^{442}$ possible encoding sequences provide tremendous flexibility to make drastic changes in the RNA genome of FMD virus (FMDV), a virus of similar size to poliovirus, while preserving the capacity to encode the same exact protein. Changes can be made in codon bias or codon pair bias, and nucleic acid signals and secondary structures in the RNA can be added or removed. Additional or novel proteins can even be simultaneously encoded in alternative frames.

Codon Pair Bias

A distinct feature of coding sequences is their codon pair bias. This may be illustrated by considering the amino acid pair Ala-Glu, which can be encoded by 8 different codon pairs and this pairing can have a bias that effects translation of human and viral genes in human cells (Table 1). If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23× 0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is a comprehensive representation of human coding sequences. Using this set of genes, the frequencies of codon usage were re-calculated by dividing the number of occurrences of a codon by the number of all synonymous codons coding for the same amino acid. As expected, the frequencies correlated closely with previously published ones such as the ones given in Table 2. Slight frequency variations are possibly due to an oversampling effect in the data provided by the codon usage database at Kazusa DNA Research Institute (www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 1 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.97 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 2; observed frequency). Frequency and observed/expected values for the amino acid pair Ala-Glu, which can be encoded by 8 different codon pairs is seen in Table 1 and the complete set of 3721 ($61^2$) codon pairs, based on the set of 14,795 human genes, (Coleman et al. 2008)

TABLE 1

Codon pair scores for the amino acid pair Alanine-Glutamine

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |
| AE | GCTGAA | 0.112 | 0.145 | 1.29 |
| AE | GCTGAG | 0.150 | 0.206 | 1.37 |
| Total | | 1.000 | 1.000 | |

TABLE 2

Codon Bias in Human Genes

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |

TABLE 2-continued

Codon Bias in Human Genes

| Amino Acid | Codon | Number | /1000 | Fraction |
|---|---|---|---|---|
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

If the ratio of observed frequency/expected frequency of the codon pair is greater than one the codon pair is said to be overrepresented. If the ratio is smaller than one, it is said to be underrepresented. In the example the codon pair GCA-GAA is overrepresented 1.65-fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

Codon pair bias was discovered in prokaryotic cells, but has since been seen in all other examined species, including humans. The effect has a very high statistical significance, and is certainly not just noise. However, its functional significance, if any, is a mystery. One proposal is that some pairs of tRNAs interact well when they are brought together on the ribosome, while other pairs interact poorly. Since different codons are usually read by different tRNAs, codon pairs might be biased to avoid putting together pairs of incompatible tRNAs. Another idea is that many (but not all) under-represented pairs have a central CG dinucleotide (e.g., GCCGAA, encoding AlaGlu), and the CG dinucleotide is systematically under-represented in mammals. Thus, the effects of codon pair bias could be of two kinds—one an indirect effect of the under-representation of CG in the mammalian genome, and the other having to do with the efficiency, speed and/or accuracy of translation. It is emphasized that the present invention is not limited to any particular molecular mechanism underlying codon pair bias.

Calculation of Codon Pair Bias

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale. Although exemplified here by the human example, this can be applied to any animal (e.g., cow, swine, and other domesticated animals).

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair. The detailed equations used to calculate CPB are disclosed in WO 2008/121992 and WO 2011/044561, which are incorporated by reference.

$$S(P_{ij}) = \ln\left(\frac{N_o(P_{ij})}{N_E(P_{ij})}\right) = \ln\left(\frac{N_o(P_{ij})}{F(C_i)F(C_j)N_o(X_{ij})}\right)$$

In the calculation, $P_{ij}$ is a codon pair occurring with a frequency of $No(P_{ij})$ in its synonymous group. $C_i$ and $C_j$ are the two codons comprising $P_{ij}$, occurring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=No(C_i)/No(X_i)$, where $No(C_i)$ and $No(X_i)$ are the observed number of occurrences of codon $C_i$ and amino acid $X_i$ respectively. $F(C_j)$ is calculated accordingly. Further, $No(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $No(P_{ij})$ over the expected number of occurrences of $N_e(P_{ij})$.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions.

The "combined" codon pair bias of an individual coding sequence was calculated by averaging all codon pair scores according to the following formula:

$$S(P_{ij}) = \sum_{i=1}^{k} \frac{S(P_{ij})l}{k-1}$$

The codon pair bias of an entire coding region is thus calculated by adding all of the individual codon pair scores comprising the region and dividing this sum by the length of the coding sequence.

Calculation of Codon Pair Bias, Implementation of Algorithm to Alter Codon-Pair Bias An algorithm was developed to quantify codon pair bias. Every possible individual codon pair was given a "codon pair score", or "CPS". CPS is defined as the natural log of the ratio of the observed over the expected number of occurrences of each codon pair over all human coding regions, where humans represent the host species of the instant vaccine virus to be recoded.

$$CPS = \ln\left(\frac{F(AB)_0}{\frac{F(A) \times F(B)}{F(X) \times F(Y)} \times F(XY)}\right)$$

Although the calculation of the observed occurrences of a particular codon pair is straightforward (the actual count within the gene set), the expected number of occurrences of a codon pair requires additional calculation. We calculate this expected number to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k} \frac{CPSi}{k-1}$$

As discussed further below, codon pair bias takes into account the score for each codon pair in a coding sequence averaged over the entire length of the coding sequence. According to the invention, codon pair bias is determined by $$CPB = \sum_{i=1}^{k} \frac{CPSi}{K-1}$$

Accordingly, similar codon pair bias for a coding sequence can be obtained, for example, by minimized codon pair scores over a subsequence or moderately diminished codon pair scores over the full length of the coding sequence.

Since all 61 sense codons and all 3721 sense codon pairs can certainly be used (and are used) in naturally occurring coding sequences, it would not be expected that substituting a single rare codon for a frequent codon, or a rare codon pair for a frequent codon pair, would have much effect. Irrespective of the precise mechanism, the data indicate that the large-scale substitution of synonymous deoptimized codons into a viral genome results in severely attenuated viruses. This procedure for producing modified viruses has been dubbed SAVE (Synthetic Attenuated Virus Engineering).

According to aspects of the invention, viral modification can be accomplished by changes in codon pair bias as well as codon bias in one or more portions of the virus's genome. However, it is expected that adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties. The work disclosed herein includes modified codon pair bias-reduced or -minimized sequences in which codons are shuffled, but the codon usage profile is unchanged.

The effects of our virus modification can be confirmed in ways that are well known to one of ordinary skill in the art. Non-limiting examples induce plaque assays, growth measurements, and reduced lethality in test animals. The instant application demonstrates that the modified viruses are capable of inducing protective immune responses in a host.

Various embodiments of the present invention provide for deoptimized modified foot and mouth virus derived from a wild-type foot and mouth virus, or a previously modified foot and mouth virus, by substituting at least one genomic region of the wild-type foot and mouth virus, or the previously modified foot and mouth virus, with a codon deoptimized region encoding the protein sequence, or encoding a protein sequence with up to 10 amino acid replacements, additions, or deletions.

Various embodiments of the present invention provide for deoptimized modified foot and mouth virus derived from a wild wild-type foot and mouth virus or a previously modified foot and mouth virus, by substituting at least one genomic region of the wild-type foot and mouth virus or the previously modified foot and mouth virus with a codon-pair deoptimized region encoding the protein sequence, or encoding a protein sequence with up to 10 amino acid replacements, additions, or deletions.

Various embodiments of the present invention provide for deoptimized modified foot and mouth virus derived from a wild-type foot and mouth virus, or a previously modified foot and mouth virus, by substituting at least one genomic region of the wild-type foot and mouth virus, or the previously modified foot and mouth virus, with a codon deoptimized and/or codon-pair deoptimized region encoding the protein sequence, or encoding a protein sequence with up to 10 amino acid replacements, additions, or deletions.

In various embodiments, codon deoptimized foot and mouth virus comprises at least 10 deoptimized codons in the at least one genomic region, wherein the at least 10 deoptimized codons are each a synonymous codon less frequently used in the foot and mouth virus. In various embodiments, the codon deoptimized foot and mouth virus comprises at least 20, 30, 40, 50, 60, 70, 80, 90, 100, 125, 150, 200, 250, 300, 400, 500, 600, or 700 deoptimized codons in in the at least one genomic region, wherein the at least 20, 30, 40, 50, 60, 70, 80, 90, 100, 125, 150, 200, 250, 300, 400, 500, 600, or 700 deoptimized codons are each a synonymous codon less frequently used in the in the foot and mouth virus. The synonymous codon less frequently used in the in the at least one genomic region is a codon that encodes the same amino acid, but the codon is an unpreferred codon by the foot and mouth virus for the amino acid.

In various embodiments, codon deoptimized foot and mouth virus comprises at least 10 deoptimized codons in the at least one genomic region, wherein the at least 10 deoptimized codons are each a synonymous codon less frequently used in the mammalian host. In various embodiments, the codon deoptimized foot and mouth virus comprises at least 20, 30, 40, 50, 60, 70, 80, 90, 100, 125, 150, 200, 250, 300, 400, 500, 600, or 700, deoptimized codons in in the at least one genomic region, wherein the at least 20, 30, 40, 50, 60, 70, 80, 90, 100, 125, 150, 200, 250, 300, 400, 500, 600, or 700 deoptimized codons are each a synonymous codon less frequently used in the in the the mammalian host. The synonymous codon less frequently used in the in the at least one genomic region is a codon that encodes the same amino acid, but the codon is an unpreferred codon by the mammalian host for the amino acid.

In various embodiments, the codon pair bias of the modified sequence is less than the codon pair bias of the parent virus, and is reduced by at least about 0.01, at least about 0.02, at least about 0.03, at least about 0.04, at least about 0.05, at least about 0.10, at least about 0.15, at least about 0.20, at least about 0.25, at least about 0.3, at least about 0.35, at least about 0.40, or at least about 0.50.

In various embodiments, the at least one genomic region is the P2 or P3 domain of a foot and mouth virus. A foot and mouth virus utilized in practicing the present disclosure can be of any strain or serotype, such as A24, A12, Asia, O1 Manisa and O1 Campos, for example. In some embodiments, such modified viruses also contain a DIVA region, such as 3B3D regions detailed herein.

Administration

The modified FMDV described herein can be administered to a mammalian subject, such as a suid or a bovid. In various embodiments, administering the deoptimized modified virus comprises administering a dose of $10^2$, $10^3$, $10^4$ or $10^5$ pfu/mammalian subject of the deoptimized modified virus. In some instances, administration comprises administering a prime dose to the mammalian subject; and administering one or more boost doses. The skilled artisan is able to determine an effective dosing regimen, but typically the prime dose and/or the one or more boost doses (if any) are administered when the mammalian subject does not have foot and mouth disease. One or more boost doses are administered when the mammalian subject does not have foot and mouth disease. In various embodiments, the one or more boost dose is administered when the mammalian subject has been exposed to foot and mouth disease.

Modified FMDV described herein can be formulated for and administered via any route of administration known in the art, including aerosol, subcutaneous, intraoral, intranasal, intramuscular, transdermal, transmucosal and/or intradermal route(s). "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical/veterinary compositions according to the invention can also contain any pharmaceutically/veterinarally acceptable carrier. "Pharmaceutically acceptable carrier" and "veterinarally acceptable carrier" as used herein refers to acceptable materials, compositions, or vehicles that are involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be acceptable in that it must be compatible with the other ingredients of the formulation. It must also be suitable for use in contact with any tissues or organs with which it may come in contact, meaning that it must not carry a risk, or has a very low risk, of toxicity, irritation, allergic response, immunogenicity, or any other complication that excessively outweighs its therapeutic benefits.

The pharmaceutical and veterinary compositions provided herein can also be encapsulated, tableted or prepared in an emulsion or syrup for oral administration. Solid or liquid carriers may be added to enhance or stabilize the composition, or to facilitate preparation of the composition. Liquid carriers include, but are not limited to, syrup, peanut oil, olive oil, glycerin, saline, alcohols and water. Solid carriers include, but are not limited to, starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical/veterinary preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical/veterinary compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical, veterinary, and pharmacological arts will be able to determine a therapeutically effective amount through routine experimentation, for instance, by monitoring a subject's response to administration of a compound and adjusting the dosage accordingly.

Typical dosages of an effective deoptimized modified foot and mouth virus can be in the ranges indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, or the responses observed in the appropriate animal models, as previously described.

Kits

The present disclosure is also directed to a kit to prophylactically and therapeutically treat subjects in need of treatment for foot and mouth disease. The kit is useful for practicing the inventive method of eliciting a protective immune response against foot and mouth virus, reducing the likelihood of having foot and mouth virus, and treating foot and mouth virus. The kit is an assemblage of materials or components, including at least one of the inventive compositions. Thus, in some embodiments the kit contains a composition including the deoptimized modified as described above.

The exact nature of the components configured in the inventive kit depends on its intended purpose. For example, some embodiments are configured for the purpose of method of eliciting a protective immune response against foot and mouth virus, other embodiments are configured for the purpose of reducing the likelihood of having foot and mouth virus, and still other embodiments are configured for the purpose of treating foot and mouth virus. In one embodiment, the kit is configured particularly for the purpose of treating mammalian subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to eliciting a protective immune response against foot and mouth virus, reducing the likelihood of having foot and mouth virus, and treating foot and mouth virus. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment.

The packaging materials employed in the kit can be those customarily utilized in vaccine therapies. As used herein, the term "package" refers to a suitable solid matrix or material such as glass, plastic, paper, foil, and the like, capable of holding the individual kit components. Thus, for example, a package can be a syringe or glass vial used to contain suitable quantities of an inventive composition containing deoptimized modified foot and mouth virus. The packaging material generally has an external label which indicates the contents and/or purpose of the kit and/or its components.

Having generally described this invention, the same will be better understood by reference to certain specific examples, which are included herein to further illustrate the invention and are not intended to limit the scope of the invention as defined by the claims.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Cells

Porcine kidney cell lines (LF-PK and IBRS-2) were obtained from the Foreign Animal Disease Diagnostic Laboratory (FADDL), Animal, Plant, and Health Inspection Service (APHIS) at the PIADC. Secondary porcine kidney (PK) cells were provided by the APHIS National Veterinary Service Laboratory, Ames, Iowa. BHK-21 cells (baby hamster kidney cells strain 21, clone 13, ATCC CL10), were obtained from the American Type Culture Collection (ATCC, Rockville, Md.). All cells were maintained as previously reported (De los Santos et al., 2009).

Viruses

FMDV A24-WT was generated from the full-length serotype $A_{24}$ Cruzeiro infectious clone ($pA_{24}$-WT) as previously described (Rieder et al 2005). A derivative of this plasmid was constructed to contain a NheI unique site in the 2A coding region (pA24 Cru-NheI). Deoptimized P2, P3 or P2/P3 clones were derived by subcloning codon modified sequences designed using the method described by Burns et al (2006) into pA24 Cru-NheI backbone. Specifically, a 1,517 bp NheI/MfeI, a 2,001 bp MfeI/BamHI or a 3512 bp NheI/BamHI fragments containing P2 and/or P3 modified sequences and DIVA markers in the 3B and 3Dpol regions (Uddowla et al., 2012) were used to substitute WT sequences in $pA_{24}$-NheI. cDNAs were linearized with SwaI and viral RNA were derived by in vitro transcription with T7 polymerase using MEGAscript T7 kit (Ambion) purified with an RNeasy (Qiagen) kit following the manufacturer's directions. 10-20 ug of viral RNAs were electroporated in BHK-21 cells as previously described (Rieder 2005) and after 24 h incubation at 37° C., cells were frozen for subsequent virus release and passage. Recovered viruses were sequenced and used for large scale preparation. Virus stocks were purified and concentrated by density gradient centrifugation in sucrose 10-50% (W/V).

A summary of all deoptimized virus designs including the method of deoptimization, the final % of CG dinucleotides and overall level of attenuation in vivo is depicted in Table 3.

TABLE 3

Deoptimized virus designs

| Name | Serotype | Deoptimization method | Attenuation | % CpG |
|---|---|---|---|---|
| A24-WT | A24 | N/A | N/A | 5.73 |
| A24-P2 deopt$_{3B3D}$ | A24-DIVA | CD | ++ (mouse) + (pig) | 6.50 |
| A24-P3 deopt$_{3B3D}$ | A24-DIVA | CD | + (mouse) + (pig) | 7.01 |
| A24 P2/P3 deopt$_{3B3D}$ | A24-DIVA | CD | ++++ (mouse) ++ (pig) | 7.79 |
| A24 P1 deopt$_{3B3D}$ | A24-DIVA | CPB (SAVE) | ++++ (mouse) ++ (pig) | 7.44 |
| ASIA P1 deopt$_{3B3D}$ | Asia1-DIVA | CPB (SAVE) | +++++ (mouse) ++ (pig) | 7.44 |

FMDV Cell Infections

Cultured cell monolayers were infected with FMDV at a multiplicity of infection (moi) of 10. After 1 h adsorption at 37° C., unabsorbed virus was removed by washing the cells with a solution containing 150 mM NaCl in 20 mM morpholineethanesulfonic acid (MES) pH=6.0, before adding MEM and proceeding with incubation at 37° C. in 5% $CO_2$. Infected cells were frozen at 1, 3, 6 and 24 h and virus titers were determined after thawing by plaque assay on BHK-21 cells. WT plaques were counted at 30 hpi and P2-P3 deopt plaques were counted at 48 hpi.

The number of VP/ml was determined by qRT-PCR using primers and probe targeting a conserved and herein unmodified 3D region of the FMDV genome and standard cycling conditions (Callahan et al 2002). Cycle threshold (Ct) values were converted to RNA copies per milliliter or milligram using the equation derived from analysis of serial 10-fold dilutions of in vitro synthesized FMDV RNA of known concentration. The number pfu/ml was determined by conventional plaque assay staining at 48 hpi (Rieder et al 1993)

Animal Experiments

Animal experiments were performed in the high-containment facilities of the Plum Island Animal Disease Center, conducted in compliance with the Animal Welfare Act (AWA), the 2011 Guide for Care and Use of Laboratory Animals, 2002 PHS Policy for the Humane Care and Use of Laboratory Animals, and U.S. Government Principles for Utilization and Care of Vertebrates Animal Used in Testing, Research and Training (IRAC 1985), as well as specific animal protocols reviewed and approved by the Institutional Animal Care and Use Committee (IACUC) of the Plum Island Animal Disease Center (USDA/APHIS/AC Certificate number: 21-F-0001; Protocol 204-14R for mice and 151-13R for swine).

Mice Experiment

C57BL/6 6-7-week-old female mice were purchased from Jackson Labs (Bar Harbor, Me.) and were acclimated for one week. To evaluate virulence, a comparison of A24-P2Deopt$_{3B3D}$, A24-P3Deopt3B3D and A24-P2/P3Deopt$_{3B3D}$ vs A24 WT. Groups of C57BL/6 mice (n=6) were anesthetized with isofluorane (Webster Veterinary, Devens, Mass.) and immediately infected subcutaneously (SC) in the left rear footpad with 50-100 ul of different doses of FMDV A24-P2Deopt$_{3B3D}$ deopt, A24-P3Deopt$_{3B3D}$, and A24-P2/P3Deopt$_{3B3D}$, or reference FMDV A24. Animals were monitored for 8 days. Viremia was determined by plaque assay or end point dilution on BHK-21 cells and serum samples were collected weekly to assess neutralizing antibody response.

Swine Experiments

In a first experiment, 23 Yorkshire gilts (five weeks old and weighing approximately 18-23 kg each) were acclimated for 1 week and were subsequently divided in 5 groups of 4 animals each and one group of 3 animals. In the 5 groups of 4 animals each, 3 animals were inoculated intradermally in the heel bulb (IDHB) of the right hind foot with $10^6$ or $10^7$ pfu/animal of FMDV A24-P2Deopt$_{3B3D}$ or A24-P3Deopt$_{3B3D}$ or A24-P2/P3Deopt$_{3B3D}$. The remaining animal of the group was a naïve animal for evaluation of contact transmission from directly inoculated animals. The 6$^{th}$ group comprised 3 animals and was inoculated with $10^5$ of FMDV A24 WT.

In a second experiment, 16 swine were divided in 4 groups of 4 animals each. Three groups were IDHB inoculated as described above but at lower doses of $10^2$, $10^3$ or $10^5$ pfu/animal of FMDV A24 P2/P3 deopt. The remaining group was inoculated with $10^3$ of FMDV WT.

Following each FMDV inoculation, clinical scores were evaluated daily for 7 days by determining the number of toes presenting FMD lesions and the presence of lesions in the snout and/or mouth. The maximum score considered was 17, and lesions restricted to the site of inoculation were not counted. The % of lymphocytes in the white cell population from whole blood collected in EDTA was measured for the first 7 days using a Hemavet cell counter (Drew Scientific-Erba Diagnostics, Miami Lakes, Fla.). Samples of serum and nasal swab were collected the day of inoculation (baseline) and daily for 7 days after inoculation.

Detection of Virus in Sera and Nasal Swabs

Mice and swine sera and swine nasal swabs were assayed for the presence of virus by plaque titration on BHK-21 cells. Virus titers were expressed as $\log_{10}$ pfu/ml of serum or nasal swab secretions. The detection level of this assay is 5 pfu/ml. In addition, FMDV RNA was detected by real-time RT-PCR (rRT-PCR) as previously described (Alejo et al., 2013). Cycle threshold (Ct) values were converted to RNA copies per milliliter using the equation derived from analysis of serial 10-fold dilutions of in vitro synthesized FMDV RNA of known concentration and expressed as the genome copy number per ml of serum or nasal swab.

Evaluation of Humoral Immune Response

Neutralizing antibody titers were determined in mice or swine sera samples by end-point titration according to the method of Kärber (OIE 2012). Antibody titers were expressed as the $\log_{10}$ value of the reciprocal of the dilution that neutralized 100 TCID$_{50}$ in 50% of the wells.

Data Analyses

Data handling, analysis and graphic representations were performed using Prism 5.0 (GraphPad Software, San Diego, Calif.) or Microsoft Excel (Microsoft, Redmond, Wash.). Statistical significance was determined using Student's t test.

Example 2

Synonymous Deoptimization of P2, P3 or P2/P3 Genomic Regions Results in Viable FMDV Previous studies have shown that sequence deoptimization of the P1 genomic region is tolerated by FMDV strain A12 (Diaz san Segundo et al, supra). The P1 region is variable from strain to strain, so in order to test if such a strategy would work for the highly conserved P2 and/or P3 regions of FMDV, we designed viral genomes in which codon usage was deoptimized by replacement with non-preferred codon. Deoptimized sequences contained 320 and/or 367 nucleotide substitutions, respectively, throughout P2 and P3 coding regions, in addition to mutations that provided negative antigenic markers in the 3B and 3Dpol viral proteins, (FIG. 1). Modified sequences were synthetically obtained from a commercial supplier and subsequently replaced into the $A_{24}$ Cruzeiro FMDV infectious cDNA clone (FIG. 2A and FIG. 2B). Electroporation of in vitro synthetized RNAs of the modified FMDV A24 derived clones in BHK-21 cells, rendered viable viruses with a yield of approximately $10^7$ pfu/ml, similarly to the WT parent. High titer viral stocks ($10^8$-$10^9$ pfu/ml) were obtained after concentration with PEG and/or purification through sucrose gradients. Repeated passage in BHK-21 cells indicated that modified viral sequences remained unchanged for at least 7 passages and no extra substitutions were detected in the original unmodified viral genome, at least as determined by consensus sequencing. In BHK-21 cells, viruses with P2 or P3 deoptimized sequences displayed a plaque morphology similar to WT, however viruses containing both, deoptimized P2 and P3, displayed a small plaque phenotype (FIG. 2C). It is known that FMDV has a relatively low specific infectivity (SI) since the ratio VP/pfu is relatively high and mostly depends on serotype and experimental purification procedures. In fact, we had previously demonstrated that deoptimization of the P1 region of FMDV A12 reduces the SI by approximately 5-fold. Analyses of the SI of A24-P2, P3 or P2/P3 deoptimized virus showed no significant differences with respect to the parental WT. SI ranged from 2,580-9,900 VP/pfu for the deoptimized viruses while a value of 4,350 VP/pfu was obtained for the WT virus grown and purified under identical experimental conditions (FIG. 2C).

Figures 3A, 3B, 3C, 3D:
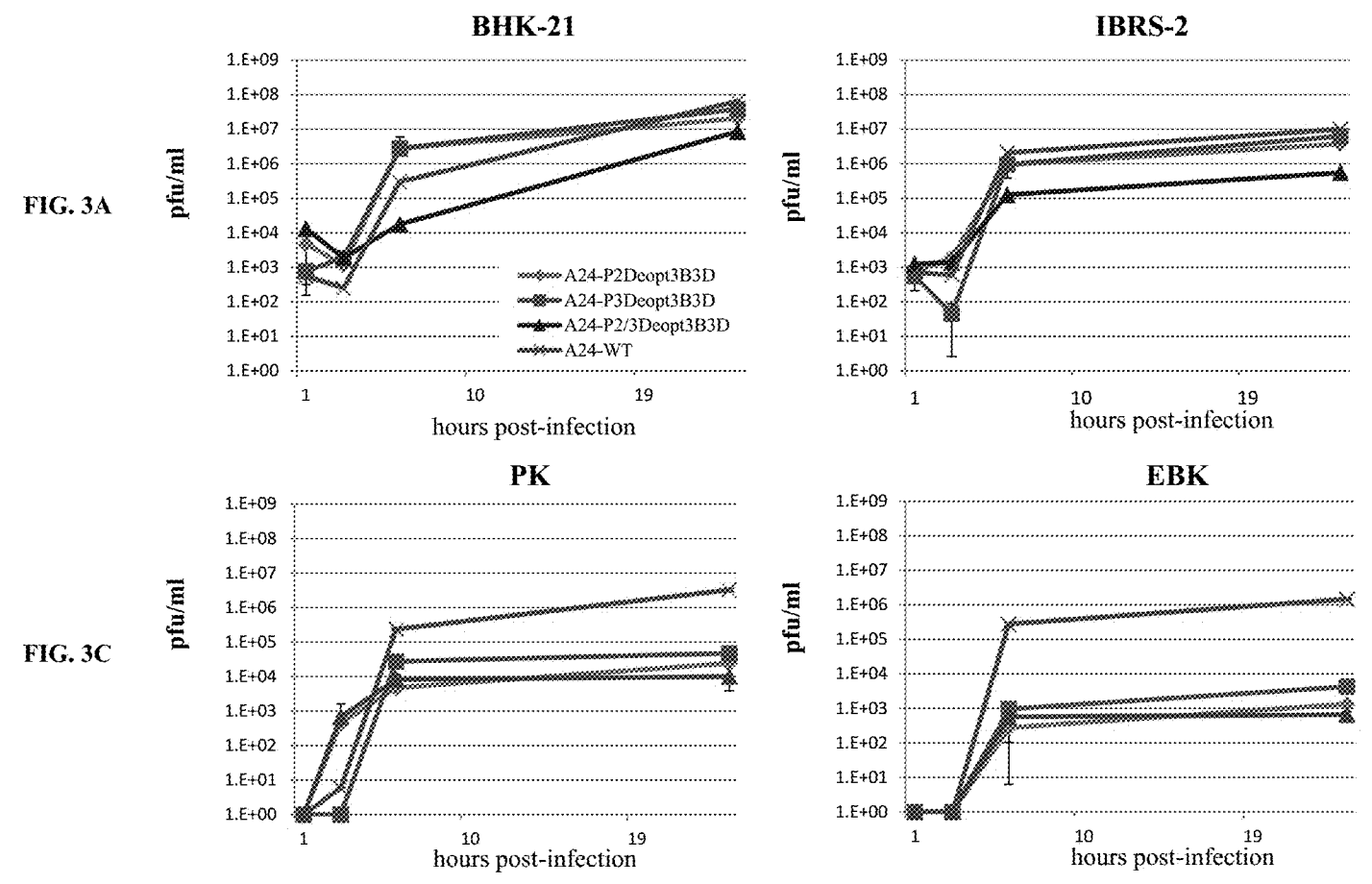

FMDV A24 with Deoptimized P2 and/or P3 Coding Regions is Attenuated in Primary Cell Cultures The phenotype of A24-deoptimized viruses was analyzed by following kinetics of growth on cell culture. Conventional cell lines used to propagate FMDV, including BHK-21 or IBRS-2, and primary porcine kidney (PK) or embryonic bovine kidney (EBK) cells, were infected with the different viruses and samples were frozen at different times post infection. Infected cells where then thawed, and titers of released viruses were determined by plaque assay on BHK-21 cells. Plaques were stained at 48 hpi to facilitate counting. As seen in FIG. 3A, by 24 hpi, the three deoptimized viruses reached end point titers of ~$10^7$ pfu/ml in BHK-21 cells, similarly to WT virus, although deoptimized A24-P2/P3Deopt$_{3B3D}$ grew at somewhat slower growth rate. A similar phenotype was detected in IBRS-2 cells but the end point titer of the A24-P2/P3Deopt$_{3B3D}$ virus was about one log lower ($10^6$ pfu/ml) in comparison to the titers of A24-WT or A24-P2Deopt$_{3B3D}$ or A24-P3Deopt$_{3B3D}$ deoptimized viruses (FIG. 3B). Interestingly all deoptimized viruses were attenuated in cells that posed selective innate pressure such as primary kidney cultures derived from swine or bovines (FIG. 3C and FIG. 3D). In these cells, the yield of all three deoptimized viruses was between 2-4 logs lower than the yield attained by WT virus. These results indicated that P2-P3 deoptimized FMDV were attenuated in cell culture and behaved similarly to other attenuated FMDV strains previously reported.

Figures 4A, 4B, 4C:
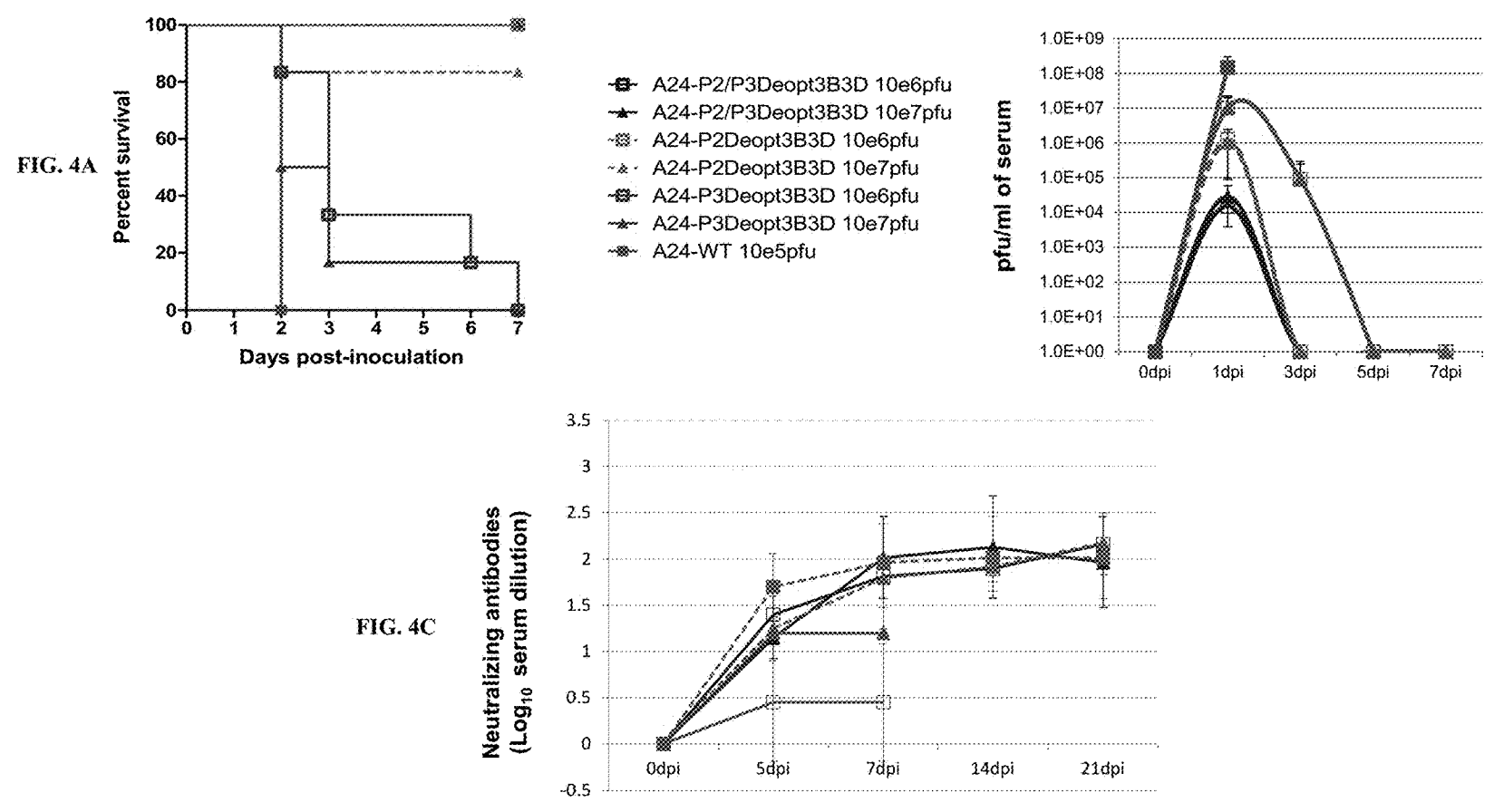

Synonymous Deoptimization of P2 and/or P3 Coding Regions Results in Attenuation of FMDV in Mice We have previously confirmed that an FMD mouse model developed for FMDV serotype C is also an efficient tool for FMDV serotype A and O. To examine the virulence of A24-P2-P3 deopt viruses 6-7 week-old female C57BL/6 mice were inoculated with different doses of FMDV A24-P2Deopt$_{3B3D}$, A24-P3Deopt$_{3B3D}$ or A24-P2/P3Deopt$_{3B3D}$ or FMDV A24-WT. Clinical signs, survival rate and the presence of virus or viral RNA in blood were monitored for a week post infection. As expected, animals inoculated with $10^5$ pfu of WT FMDV A24 developed clinical signs, including lethargy and rough fur (data not shown), and died by 24-48 h post inoculation (FIG. 4A). In contrast, animals inoculated with deoptimized A24 viruses displayed different levels of survival depending on the virus variant and the dose. Interestingly, all animals inoculated with A24-P2/P3Deopt$_{3B3D}$, independently of the dose used, animals inoculated with A24-P2Deopt$_{3B3D}$ at $10^6$ pfu, and 80% of the animals inoculated with $10^7$ pfu of A24-P2Deopt$_{3B3D}$ did not show clinical signs or died by one week post inoculation (FIG. 4A), while the group of mice inoculated with A24-P3Deopt$_{3B3D}$ did not survive, although disease progression was significantly slower than inoculation with WT FMDV A24. Consistently with the survival data, animals inoculated with A24-P2/P3Deopt$_{3B3D}$ virus developed the lowest viremia levels (in the order of $10^4$ pfu/ml), followed by A24-P2Deopt$_{3B3D}$ ($10^6$ pfu/ml), A24-P3Deopt$_{3B3D}$ ($10^7$ pfu/ml) and A24-WT ($10^8$ pfu/ml) (FIG. 4B). All inoculated animals inoculated with the deoptimized variants developed high levels of neutralizing antibody titers, about 2 log 10 by 7-15 dpi that were boosted after challenge with WT virus at 21 dpi (FIG. 4C). Directly correlated with the seroneutralization data, all animals that survived the initial inoculation with the A24 deoptimized mutants were completely protected after challenge with a lethal dose of A24 WT virus, and did not develop detectable viremia (data not shown). These results indicate that FMDV A24-P$^2$/and/or P3 deoptimized viruses were attenuated in mice and elicited a strong protective humoral response against challenge with WT virus.

Synonymous Deoptimization of P2 and/or P3 Coding Regions Results in Attenuation of FMDV in Swine The promising results obtained in mice prompted us to evaluate virulence of A24-P2Deopt$_{3B3D}$, A24-P3Deopt$_{3B3D}$ and A24-P2/P3Deopt$_{3B3D}$ in swine, FMDV natural host. Groups of three pigs were inoculated IDHB in the rear heel bulb with $10^6$ or $10^7$ pfu/animal of A24-P2Deopt$_{3B3D}$ and A24-P2/P3Deopt$_{3B3D}$. Given the relatively low attenuation observed in vitro and in mice for the A24-P3Deopt$_{3B3D}$ virus, only a group inoculated with $10^6$ pfu/animal was included. A naïve contact animal was included in each group and remain in contact for the duration of the experiment. We also included one extra group inoculated with $10^5$ pfu of A24-WT virus as control.

Figure 6:
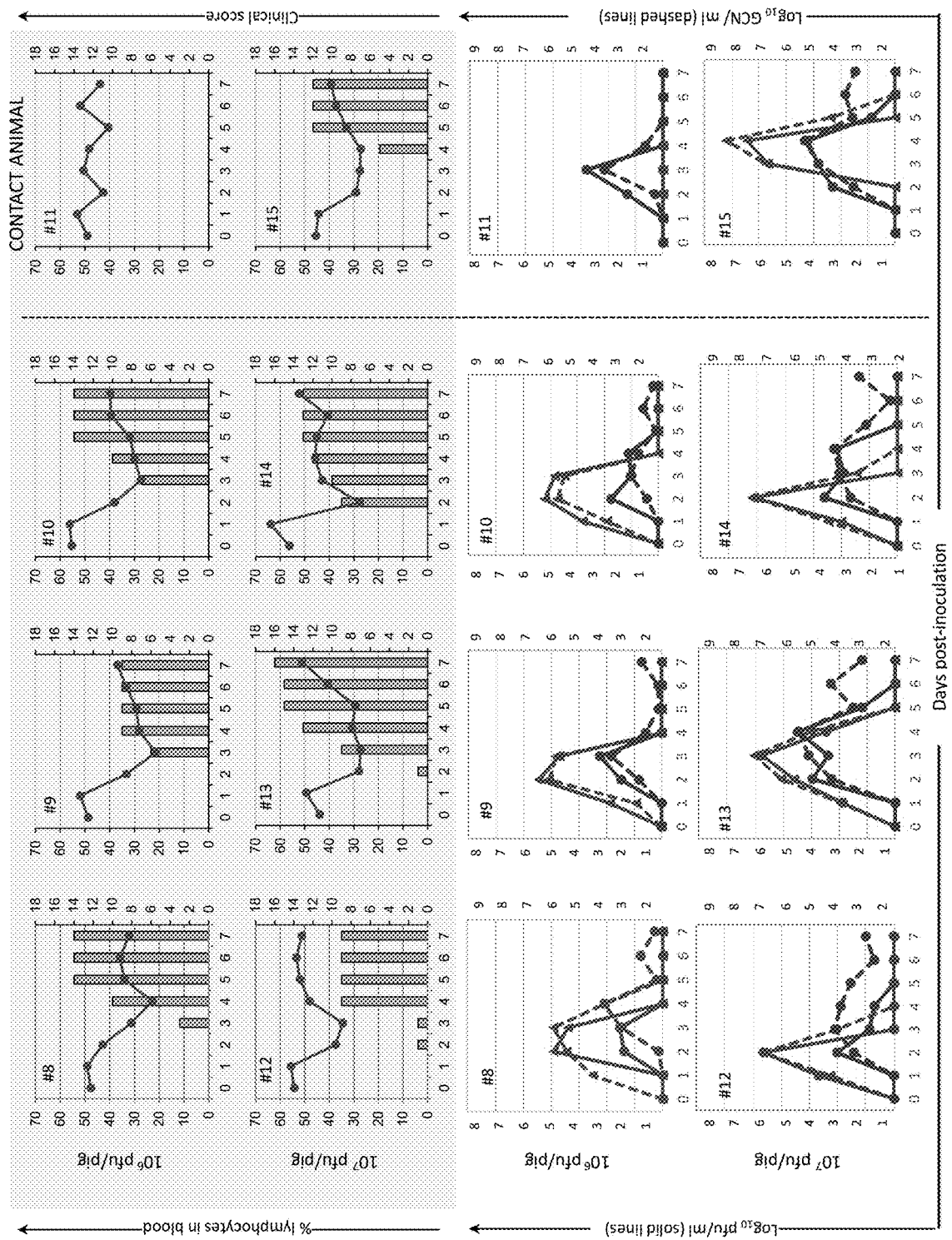
FIG. 6 depicts clinical outcome in animals inoculated with A24-P2Deopt$_{3B3D}$. 18-23 kg castrated male Yorkshire swine (n=3/group) were inoculated with $10^6$ plaque forming units (pfu) [animals 8 to 10] or $10^7$ pfu [animals 12 to 14] of FMDV A24-P2Deopt$_{3B3D}$. One naïve animal [#11 and #15] was housed in contact with each group throughout the duration of the experiment. Animals were monitored for 7 days and samples of heparinized blood, serum and nasal swabs were collected daily. Clinical score (blue bars) and % of lymphocytes (green line) for each animal are represented in the top panels; Virus isolation in serum (red line) and nasal secretion (blue line) and presence of viral copy numbers (GCN) per ml of serum (red dashed line) and nasal secretion (blue dashed line) are presented in the bottom panels.
Figure 7:
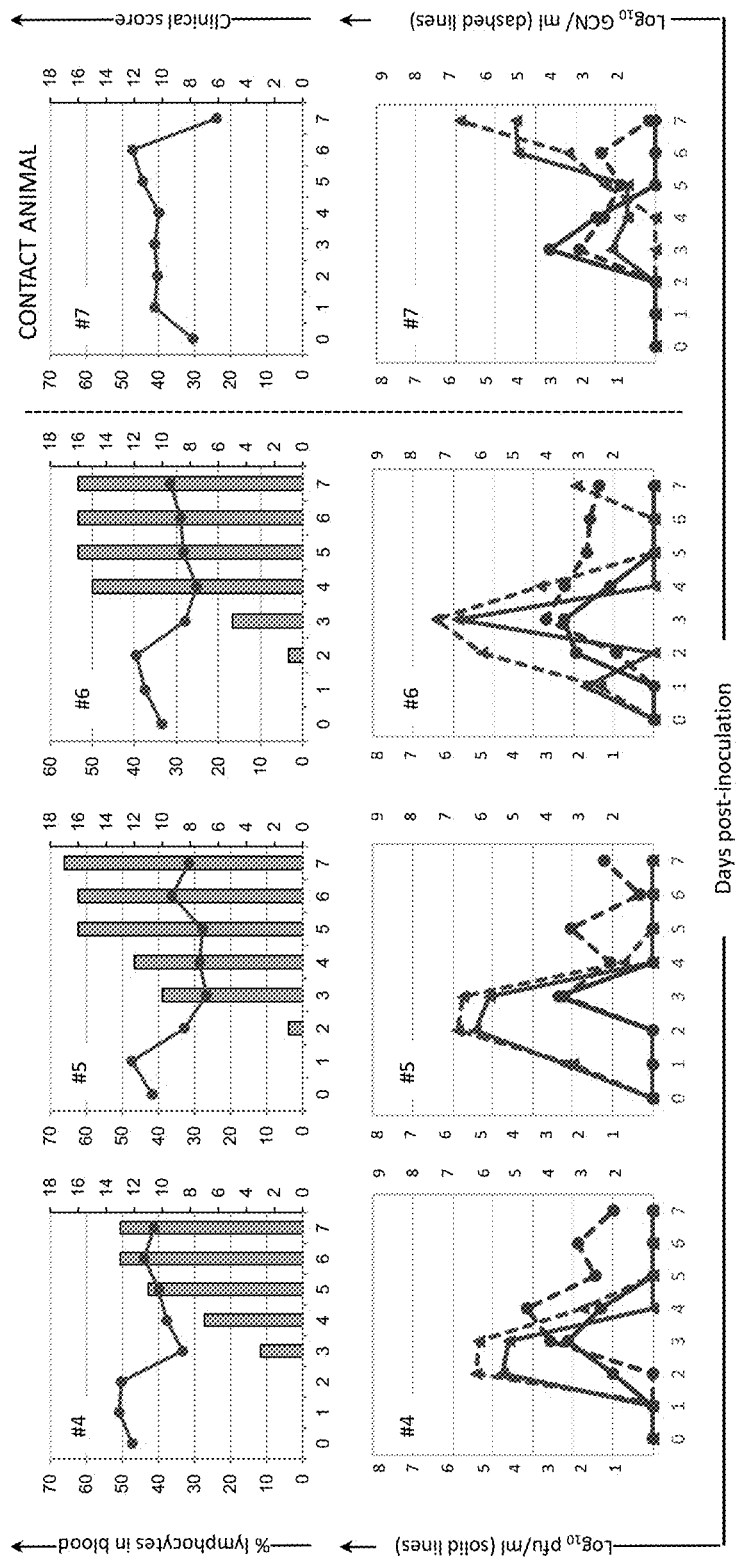
FIG. 7 depicts clinical outcome in animals inoculated with A24-P3Deopt$_{3B3D}$. 18-23 kg castrated male Yorkshire swine (n=3/group) were inoculated with $10^6$ plaque forming units (pfu) of FMDV A24-P3Deopt$_{3B3D}$. One naïve animal [#7] was in contact with the inoculated pigs throughout the duration of the experiment. Animals were monitored for 7 days and samples of heparinized blood, serum and nasal swabs were collected daily. Clinical score (blue bars) and % of lymphocytes (green line) for each animal are represented in the top panels; Virus isolation in serum (red line) and nasal secretion (blue line) and presence of viral copy numbers (GCN) per ml of serum (red dashed line) and nasal secretion (blue dashed line) are presented in the bottom panels.
Figure 8:
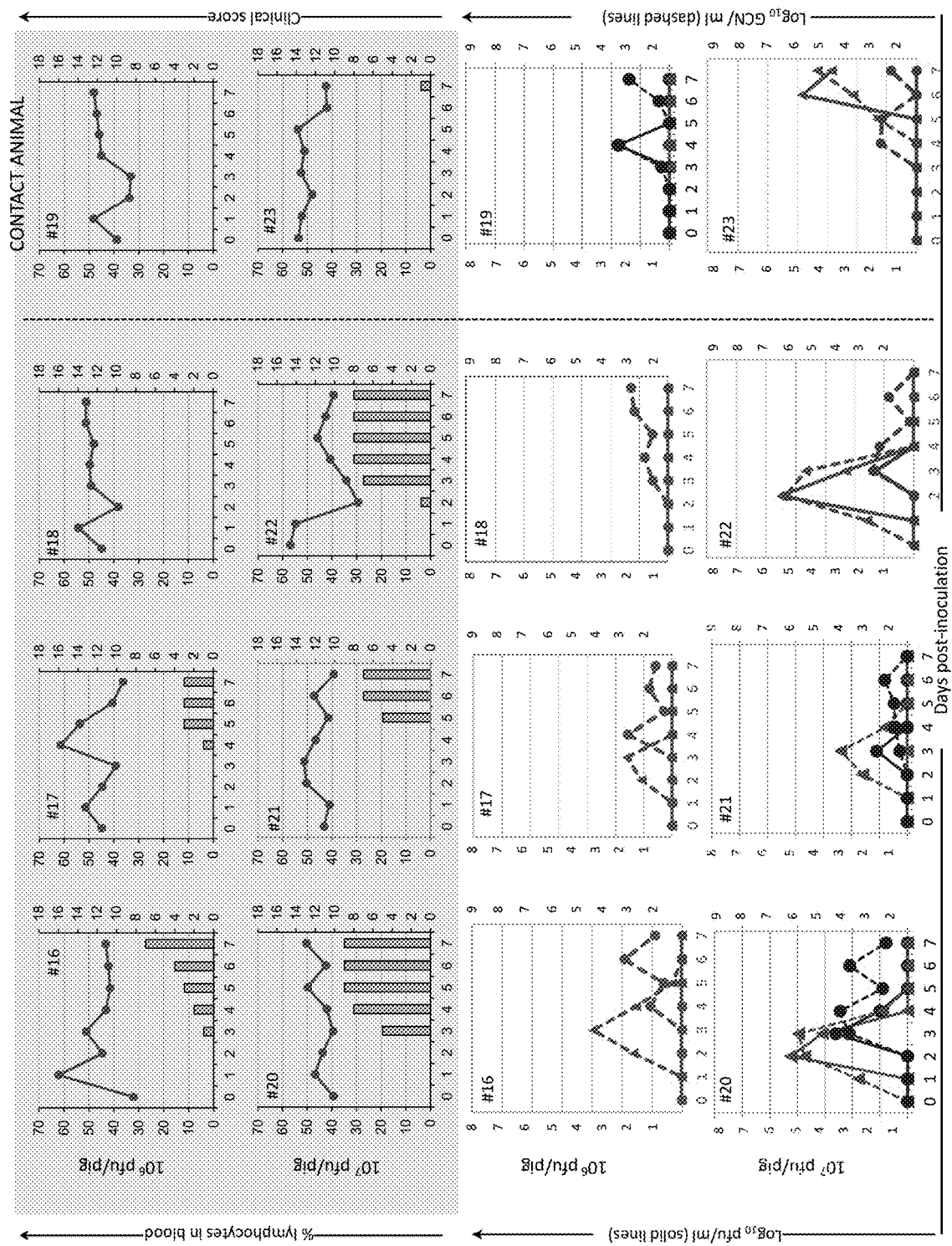
FIG. 8 depicts clinical outcome in animals inoculated with A24-P2/P3Deopt$_{3B3D}$. 18-23 kg castrated male Yorkshire swine (n=3/group) were inoculated with $10^6$ plaque forming units (pfu) [animals 16 to 18] or $10^7$ pfu [animals 20 to 22] of FMDV A24-P2/P3Deopt$_{3B3D}$. One naïve animal [#19 and #23] was housed in contact with each group throughout the duration of the experiment. Animals were monitored for 7 days and samples of heparinized blood, serum and nasal swabs were collected daily. Clinical score (blue bars) and % of lymphocytes (green line) for each animal are represented in the top panels; Virus isolation in serum (red line) and nasal secretion (blue line) and presence of viral copy numbers (GCN) per ml of serum (red dashed line) and nasal secretion (blue dashed line) are presented in the bottom panels.

All animals inoculated with $10^5$ pfu of A24-WT virus developed clinical signs by 2-3 dpi reaching high scores (10-17 lesions) between days 3-7 post inoculation, and virus was detected in serum and nasal secretion either by virus isolation or by real time PCR (FIG. 5). Animals inoculated with 10× more virus, $10^6$ pfu/animal, of A24-P3Deopt$_{3B3D}$ behaved similarly to WT (FIG. 6). However, a delay of one day in the appearance of disease was observed in animals inoculated with A24-P2Deopt$_{3B3D}$ virus, in which animals did not show clinical disease until day 3 when inoculated with $10^6$ pfu/pig (FIG. 7). Interestingly, animals inoculated with A24-P2/P3Deopt$_{3B3D}$ displayed a significantly reduced severity of disease (2-7 lesions) and one animal did not develop any clinical sign (FIG. 8). Remarkably, naïve animals maintained in contact with the animals directly inoculated with $10^6$ pfu/animal of either one of the three deoptimized FMDV variants did not develop clinical signs of disease. Consistently, viremia was detected in all animals that develop lesions but only in the naïve contact animal that was cohoused with A24-P3Deopt$_{3B3D}$. Virus was detected in nasal secretions of all animals, inoculated or in contact, but at significantly low levels in animals that did not display lesions (FIGS. 5-8). These results indicated that deoptimization of P2 or P3 coding regions results in viruses that are attenuated in swine but with highest levels of attenuation are achieved when deoptimization of both, P2 and P3 regions, is included simultaneously in the modified strain.

Figure 9:
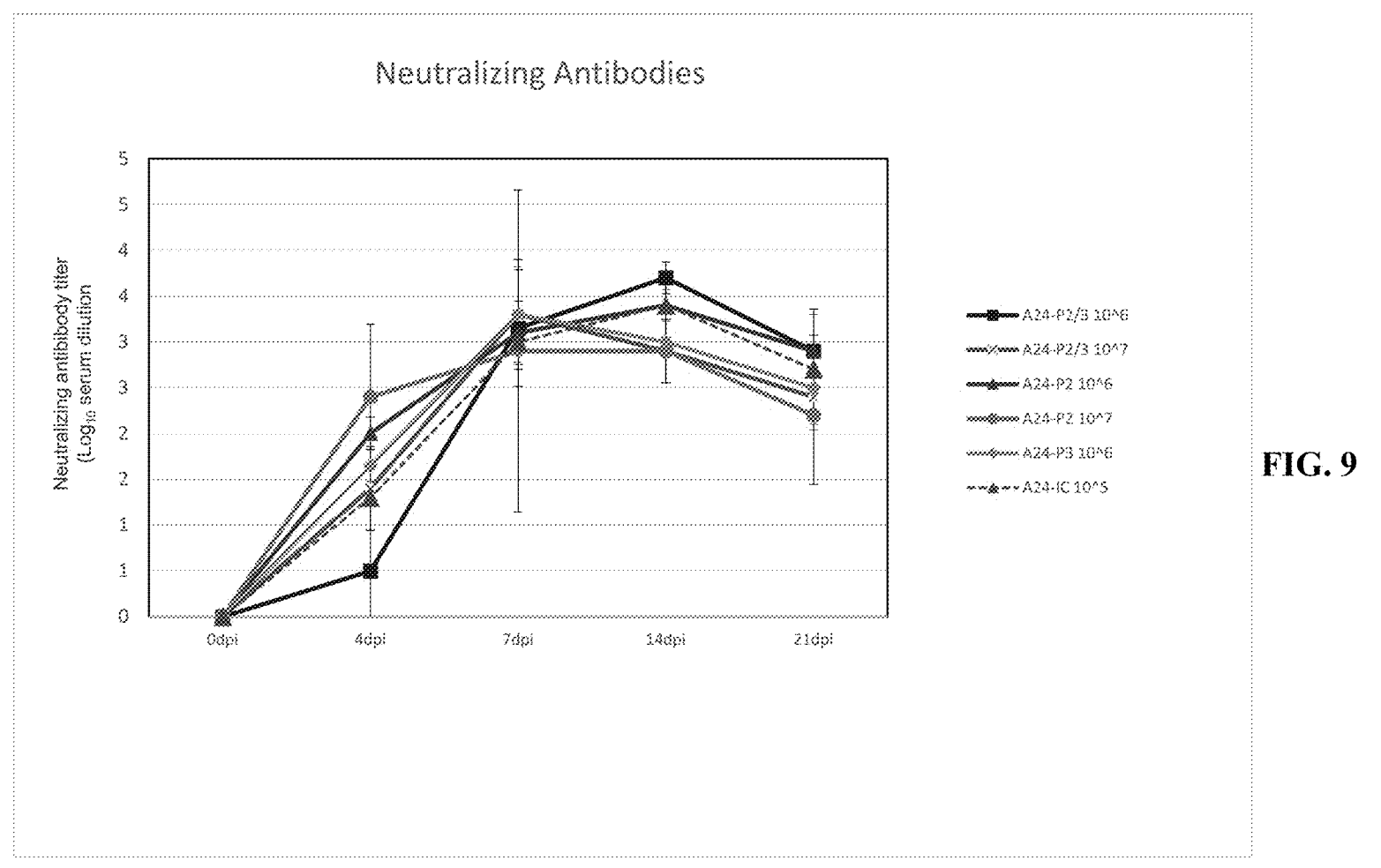

Analysis of specific neutralizing antibodies throughout the experiment showed a strong response in all animals inoculated with $10^6$ or $10^7$ pfu of A24-P2Deopt$_{3B3D}$, $10^6$ or $10^7$ pfu of A24-P3Deopt$_{3B3D}$ and $10^7$ pfu of A24-P2/P3Deopt$_{3B3D}$, and similar to the group of pigs inoculated with $10^5$ pfu of A24 WT, consistent with slow replication of the deoptimized virus in the animal host (FIG. 9).

Figure 10:
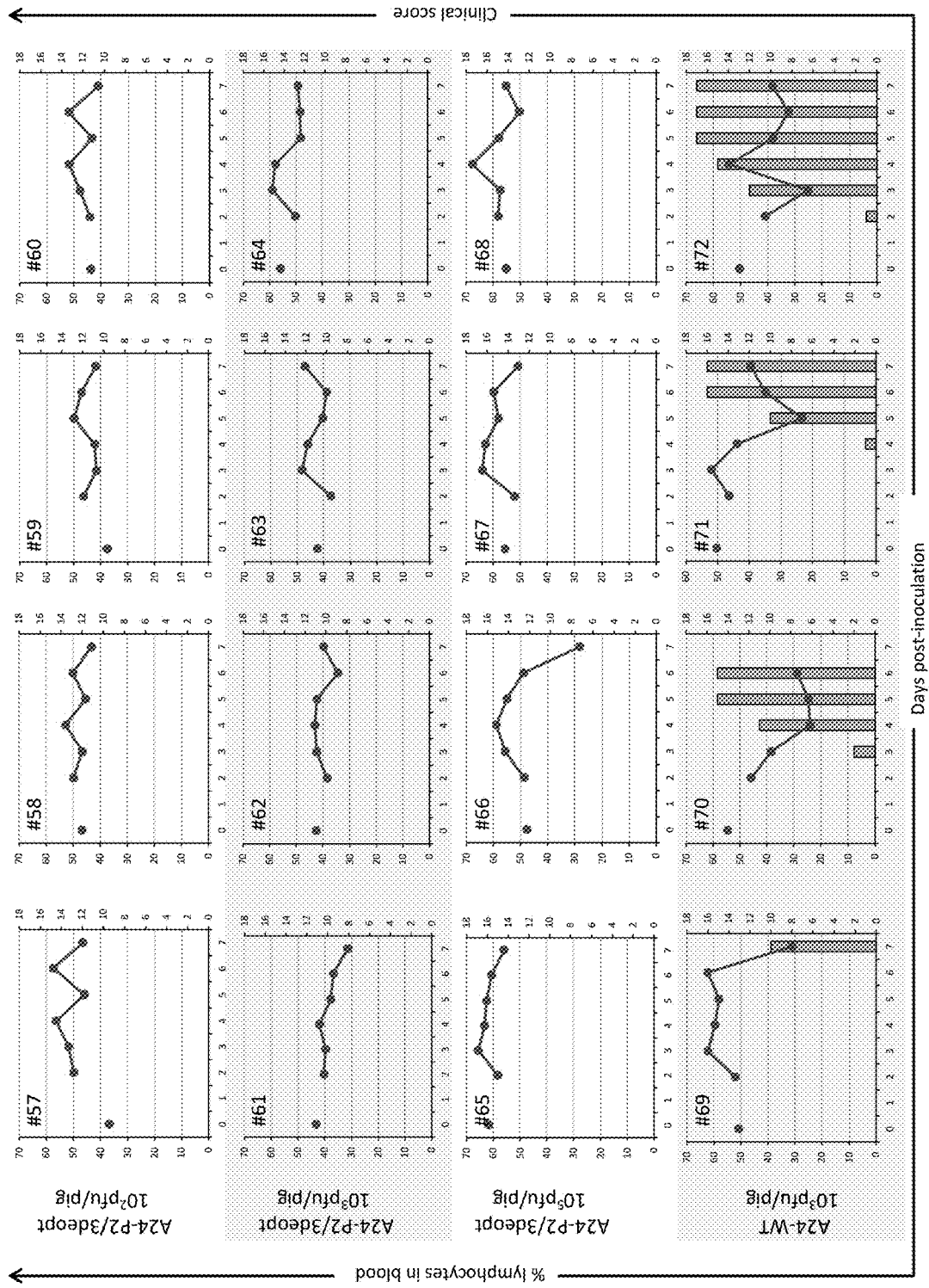
FIG. 10 depicts clinical outcome in swine inoculated with low doses of A24-P2/P3Deopt$_{3B3D}$. 18-23 kg castrated male Yorkshire swine (n=4/group) were inoculated with $10^2$, $10^3$, or $10^5$ pfu/animal of FMDV A24-P2/P3Deopt$_{3B3D}$. An additional group was inoculated with $10^3$ pfu/animal of FMDV A24 WT as control. Animals were monitored for 7 days. Clinical score (blue bars) and % of lymphocytes (green line) for each animal was determined daily.
Figure 11:
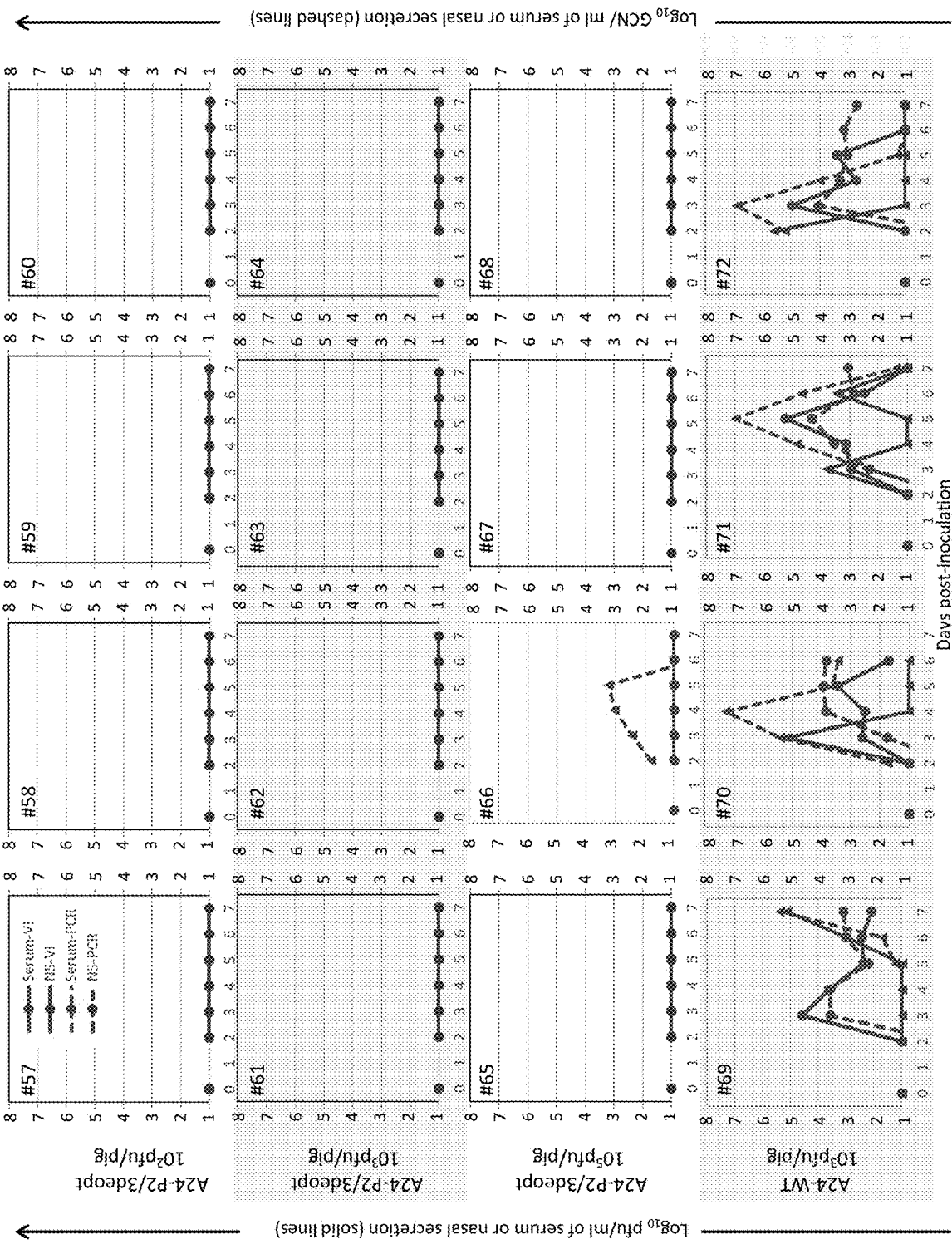
FIG. 11 depicts determination of virus or viral RNA in serum and nasal secretions of animals inoculated with low doses A24-P2/P3 Deopt$_{3B3D}$. The amount of virus was detected by virus isolation in serum (red line) and nasal secretions (blue line). The presence of viral RNA was measured by qPCR and expressed as genome copy numbers (GCN) per ml of serum (red dashed line) or per ml of nasal secretions (blue dashed line).

Given that the highest levels of attenuation were achieved in the A24-P2/P3Deopt$_{3B3D}$ variant, a second animal experiment was performed to determine the minimum infectious dose. Groups of animals were inoculated with $10^2$, $10^3$ of $10^5$ of A24-P2/P3Deopt$_{3B3D}$ virus and one group was inoculated with $10^3$ pfu/animal of A24-WT as control. As seen if FIG. 10, none of the animals inoculated with A24-P2/P3Deopt$_{3B3D}$ virus developed clinical signs by 7 days IDHB inoculation. In contrast, all swine inoculated with $10^3$ pfu/animal of A24 WT developed disease. Despite the relative low amount of inoculated A24 WT, three of the four inoculated animals of this group reached high scores (15-17 lesions. Max=17) by 5-7 dpc and one animal had a score of 10 lesions by day 7, resembling the kinetics observed in the first swine experiment using a dose 10× higher ($10^4$ pfu/animal). A consistent lymphopenia was observed in all animals that developed lesions. However, although none of the animals inoculated with A24-P2/P3Deopt$_{3B3D}$ developed vesicular lesions, one animal (#66) had detectable lymphopenia by 7 dpi but no lesions had appeared by 14 dpi (data not shown). Consistently, virus or viral RNA were detected in serum and nasal swabs of all animals inoculated with A24WT virus, while no virus or viral RNA were detected in serum or nasal secretions in all animals inoculated with A24-P2/P3Deopt$_{3B3D}$ (FIG. 11), except from animal #66 that showed lymphopenia at 7 dpi, as indicated above. However, live virus was not isolated from serum of this animal, consistent with the lack of lesions detection.

Figure 12:
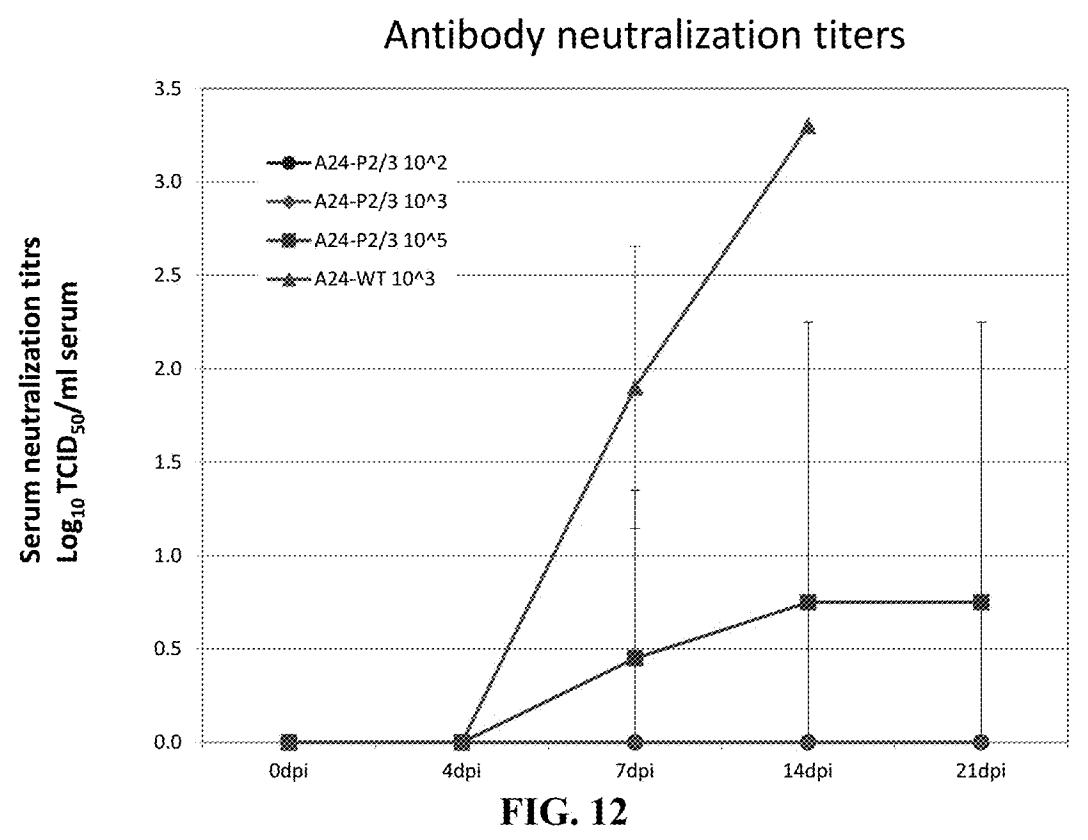

Analysis of specific neutralizing antibody response throughout the experiment in these animals showed a mild response in the group of pigs inoculated with $10^5$ pfu of A24-P2/P3Deopt$_{3B3D}$, while presence of neutralizing antibodies was undetectable in the animals inoculated with lower doses (FIG. 12). As expected, animals inoculated with FMDV A24 WT developed neutralizing antibodies starting at 7 dpi showing a slight delay as compare to animals inoculated with higher doses of WT virus (data not shown). Our data indicate that there is a dose response induction of adaptive immune response.

Example 3

Figures 16A, 16B:
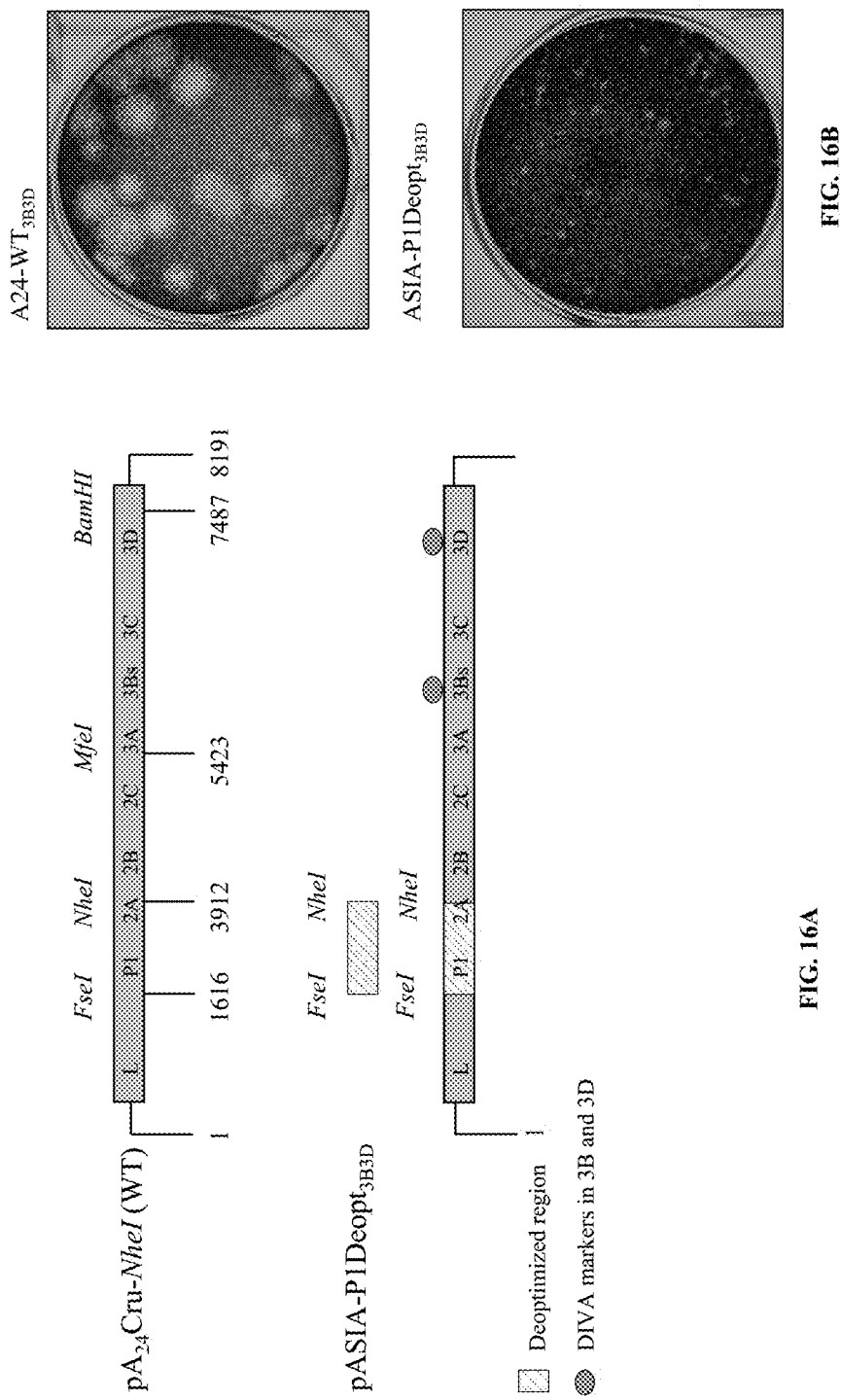
FIG. 16A and FIG. 16B depict generation of ASIA-P1 Deopt$_{3B3D}$ virus.
Figures 17A, 17B:
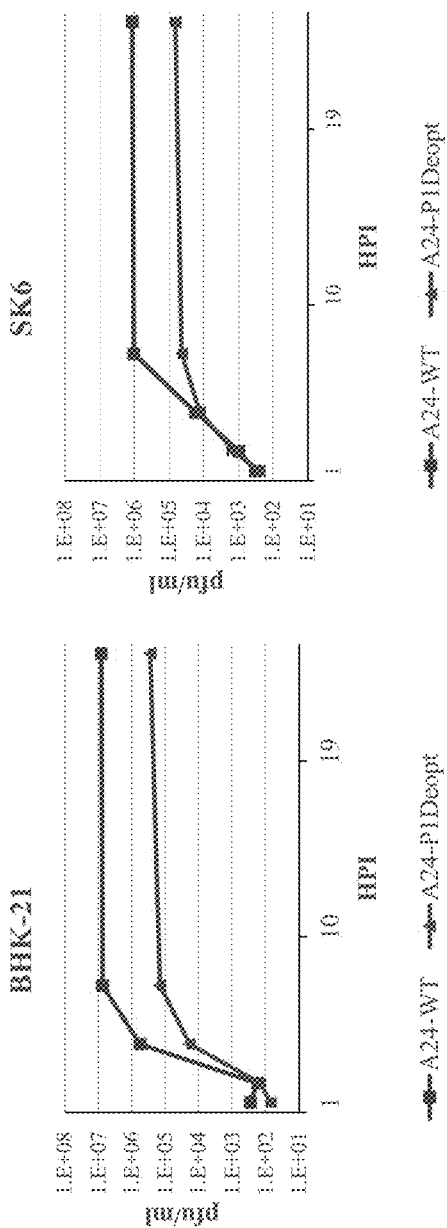
FIG. 17A and FIG. 17B depict kinetics of growth of A24 and Asia 1 P1 deoptimized FMDV.

Synonymous Deoptimization of P1 can be Extended to Multiple FMDV Serotypes/Subtypes We had previously demonstrated that codon pair bias deoptimization of P1 could be applied to FMDV serotype A (A12) rendering a viable virus attenuated in mice and swine (Diaz-San Segundo et al, supra). In order to determine whether this approach could be extended to other FMDV serotypes/subtypes, we applied the same algorithm to deoptimize the P1 regions of FMDV A24 (FIG. 13) and FMDV Asia 1 (FIG. 14). Synthetic A24 and Asia1 P1 deopt sequences were procured and cloned in pA24Cru3B3D using the conveniently engineered FseI/NheI restriction sites (FIG. 15A and FIG. 16A) Virus was rescued in BHK-21 cells showing a relatively small plaque size as compared to the respective A24 or Asia 1 wild type viruses. (FIG. 15B and FIG. 16B). Analysis of growth kinetics suggested that both viruses were attenuated in BHK-21 and in porcine SK6 cells (FIG. 17A and FIG. 17B) suggesting that deoptimization of P1 caused a delay in virus production, presumably due to an effect on virus replication or translation (Lauring et al, Cell Host Microbe., (2012) 12:623-632.; Yu et al., 2015, Molecular Cell (2015) 59:744-754).

Figures 18A, 18B, 18C:
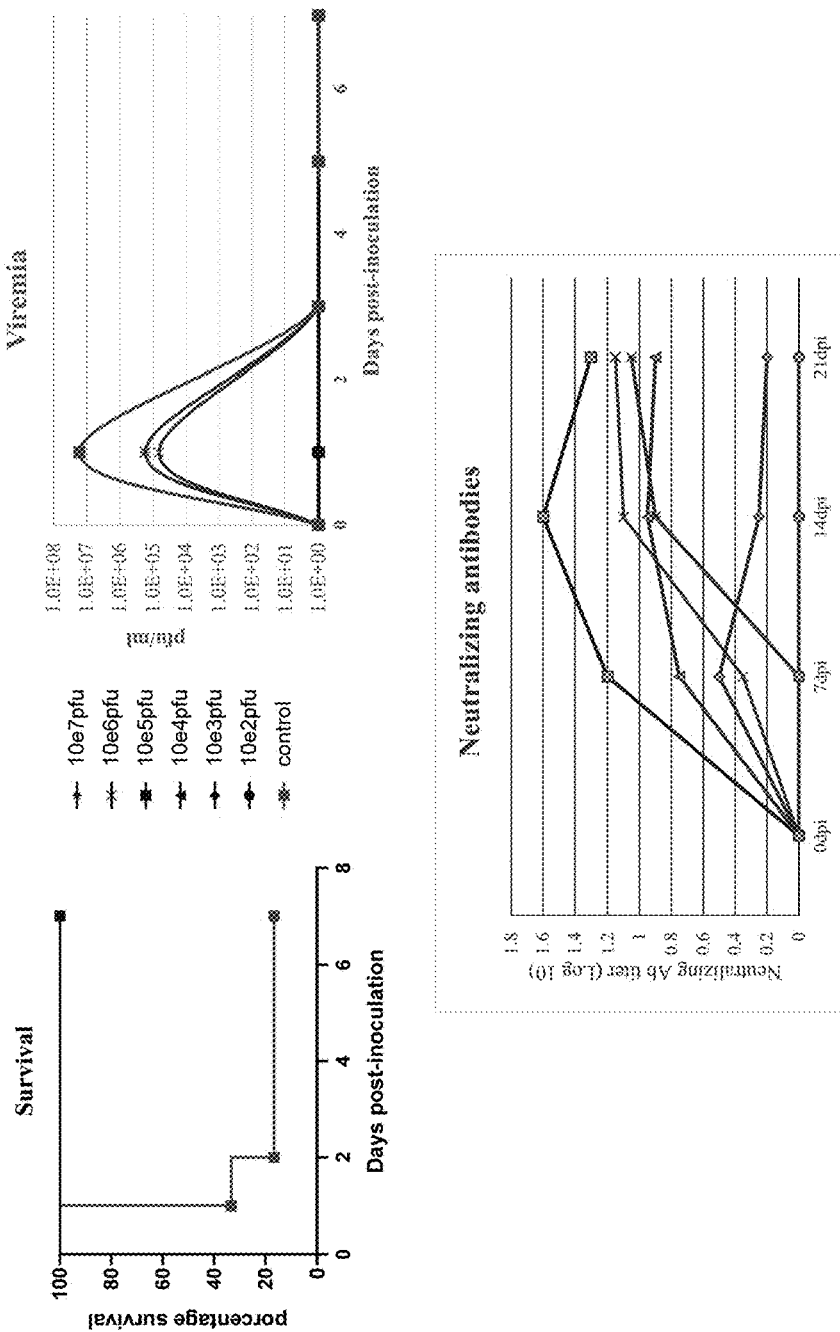
FIG. 18A, FIG. 18B, and FIG. 18C depict A24-P1 Deopt$_{3B3D}$ virus attenuation in vivo in mice. 6 to 7 weeks old female C57BL/6 mice (n=6/group) were subcutaneously inoculated in the footpad with A24-P1 Deopt$_{3B3D}$, at the indicated doses (pfu/animal).

Synonymous Deoptimization of A24cru WT 3B3D P1 Coding Region Results in Attenuation of FMDV in Mice To examine the intraserotype reproducibility of FMDV virulence in vivo, we first performed a mice experiment with A24-P1 deopt3B3D FMDV. Clinical signs, survival rate and the presence of virus or viral RNA in blood were monitored for a week post infection. As expected and consistent with previous experiments (Diaz-San Segundo 2012, J Virol. 87:5447-5460-), 83% of mice inoculated with $10^5$ pfu of FMDV A24 WT, died by 1-2 dpi; one animal died at 6 dpi (FIG. 18A). In contrast, all animals inoculated with A24 P1deopt3B3D survived for 7 days even those inoculated with $10^7$ pfu. Interestingly, only the control animals and those inoculated with $10^6$ and $10^7$ pfu developed viremia but at levels lower than those detected in the control group which had been inoculated with $10^5$ pfu of FMDV A24WT (FIG. 18B). All inoculated animals inoculated A24 P1deopt3B3D developed detectable levels of neutralizing antibody with titers oscillating between 0.2 to 1.2 log 10 depending on the amount of inoculated virus (FIG. 18C). Highest titers were detected for the control group inoculated with A24WT virus. These results were consistent with previous results obtained for FMDV A12 P1 deopt (Diaz-San Segundo et al 2015. J Virol. 90:1298-1310) indicating that P1 deoptimization of FMDV A24 results in similar attenuation in mice eliciting a detectable humoral response.

Figure 19:
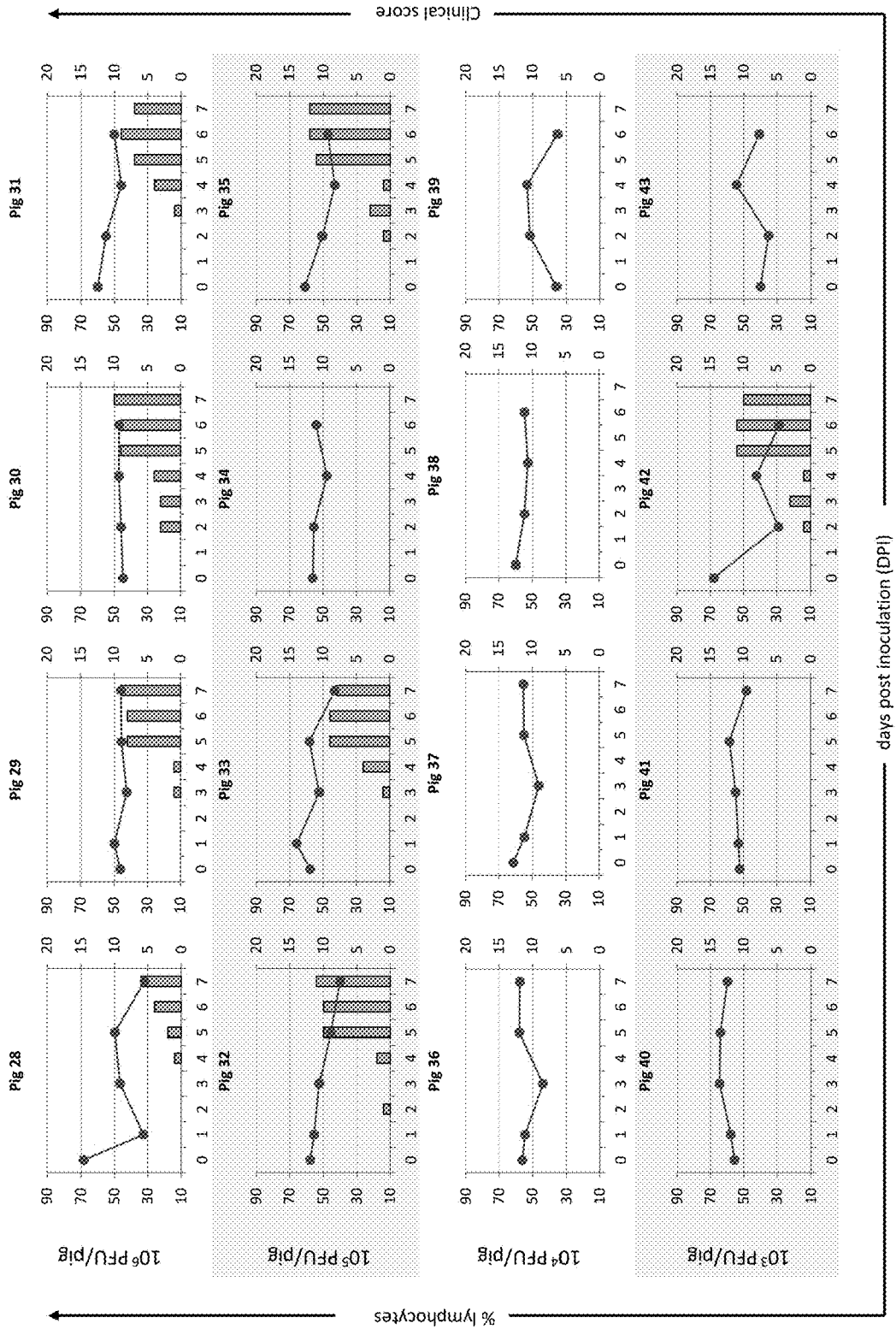
FIG. 19 depicts clinical outcome in animals inoculated with A24-P1 Deopt$_{3B3D}$. 18-23 kg castrated male Yorkshire swine (n=4/group) were inoculated with $10^6$ plaque forming units (pfu) [animals 28 to 31], $10^5$ pfu [animals 32 to 35], $10^4$ pfu [animals 36 to 39] or $10^3$ pfu [animals 40 to 43] of FMDV A24-P1 Deopt$_{3B3D}$. Animals were monitored for 7 days and samples of heparinized blood, serum and nasal swabs were collected every other day. Clinical score (blue bars) and % of lymphocytes (green line) for each animal are represented
Figure 20:
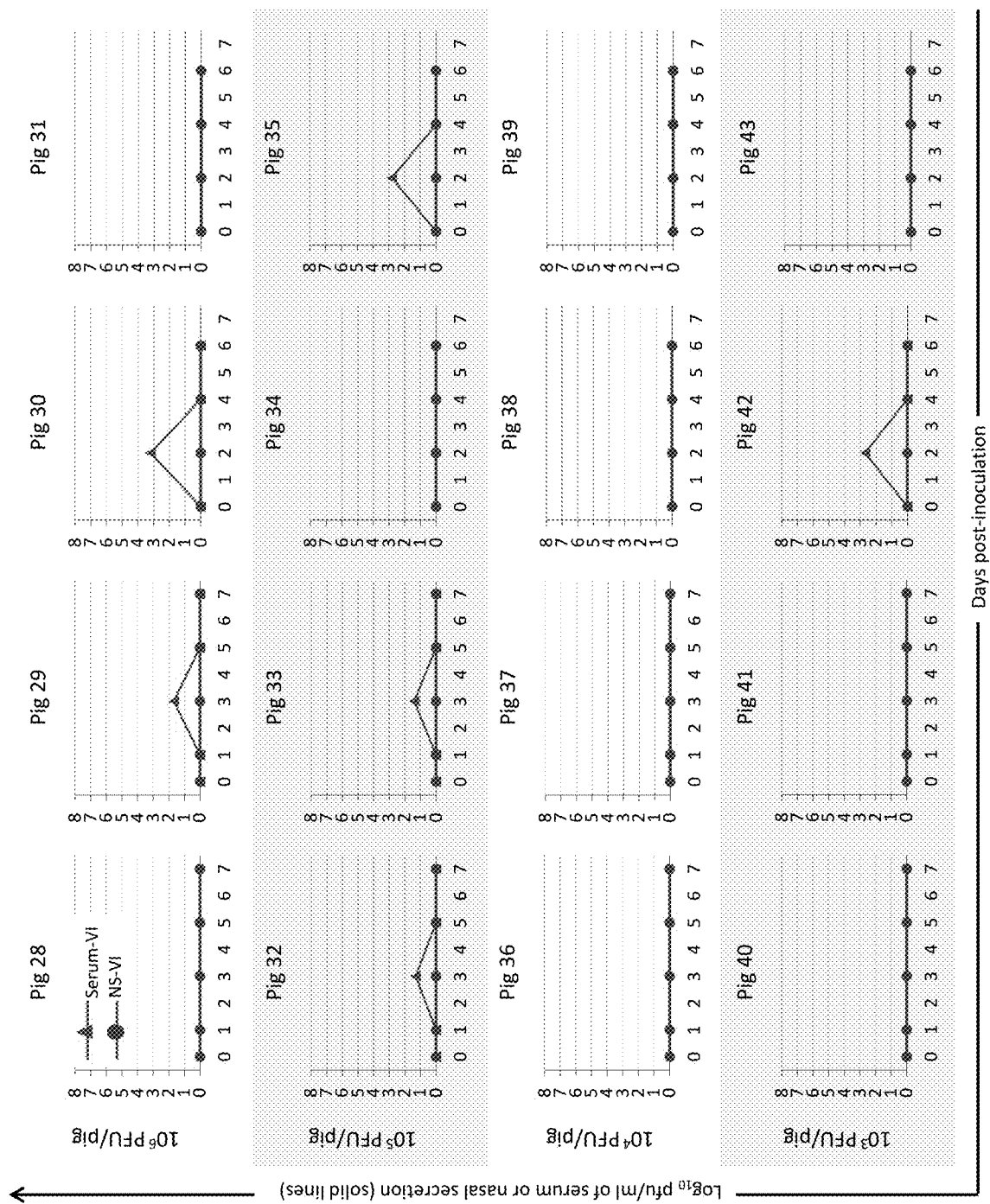
FIG. 20 depicts the determination of virus in serum and nasal secretions of animals inoculated with A24-P1 Deopt$_{3B3D}$. 18-23 kg castrated male Yorkshire swine (n=4/group) were inoculated with $10^3$, $10^4$, $10^5$, or $10^6$ pfu of FMDV A24-P1 Deopt$_{3B3D}$. Animals were monitored for 7 days and samples of serum and nasal swabs were collected daily. The amount of virus was detected by virus isolation in serum (triangle) and nasal secretions (circle). Determination of FMDV neutralizing antibodies in the serum of animals inoculated with A24-P1 Deopt$_{3B3D}$. Presence of FMDV neutralizing antibodies was evaluated by a microtiter neutralization assay on BHK-21 cells in sera of animals inoculated with different doses of A24-P1 Deopt$_{3B3D}$ or with A24Cru wild type (control) at the indicated time points after inoculation. Titers are reported as the log 10 of the reciprocal of the highest dilution of serum that neutralized the virus in 50% of the wells. Each data point represents the mean±standard deviation (SD) of each group.
Figure 21:
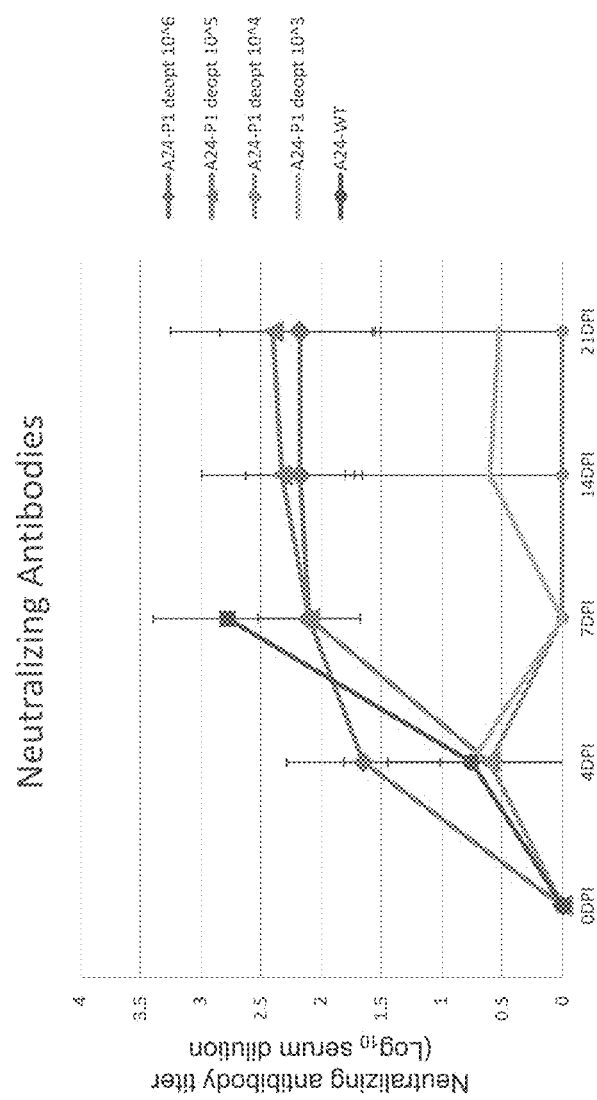
FIG. 21 depicts determination of FMDV neutralizing antibodies in the serum of animals inoculated with A24-P1 Deopt$_{3B3D}$. Presence of FMDV neutralizing antibodies was evaluated by a microtiter neutralization assay on BHK-21 cells in sera of animals inoculated with different doses of A24-P1 Deopt$_{3B3D}$ or with A$_{24}$Cru wild type (control) at the indicated time points after inoculation. Titers are reported as the log$_{10}$ of the reciprocal of the highest dilution of serum that neutralized the virus in 50% of the wells. Each data point represents the mean±standard deviation (SD) of each group.

Synonymous Deoptimization of A24cru WT 3B3D P1 Coding Region Results in Attenuation of FMDV in Swine The virulence of FMDV A24 P1deopt3B3D was further evaluated in swine. Groups of 4 pigs were inoculated IDHB in the rear heel bulb with doses varying from $10^3$ to $10^6$ pfu/animal of A24-P1Deopt3B3D. Except for one, all animals inoculated with $10^3$ and $10^4$ pfu/animal did not develop clinical signs. Animals inoculated with $10^6$ pfu of A24-P1Deopt$_{3B3D}$ virus did develop clinical signs by 2-4 dpi but with lower scores (1-10 lesions) (FIG. 19) than those observed for A24 WT virus (10-17 lesions) (FIG. 5). Interestingly, in the group inoculated with $10^5$ pfu, one animal did not develop lesions. Overall, low viremia was detected in some animals but not in nasal secretions (FIG. 20) Analysis of neutralizing antibody titers indicated that significant levels (>2 log 10 TCID50/ml) were elicited in the animals inoculated with the highest doses of virus ($10^5$ and $10^6$ pfu) (FIG. 21).

Synonymous Deoptimization of Asia 3B3D P1 Coding Region Results in Attenuation of FMDV in Mice Similar animal experiments were performed with Asia P1Deopt3B3D. Groups of mice were inoculated with $10^2$ to $10^7$ of Asia1-P1Deopt3B3D virus and one group was inoculated with $5 \times 10^4$ pfu/animal of Asia-WT as control. This dose had been earlier established as appropriate to cause 100% lethality in C57/BL6 mice. As seen if FIG. 22, none of the animals inoculated with Asia1P1Deopt3B3D virus died by 7 dpi. In contrast, all mice inoculated with Asia1 WT died by 1-2 dpi. None of the animals inoculated with Asia1P1Deopt3B3D, even those that received $10^7$ pfu/animal developed viremia while the control animals did. Interestingly, high levels of neutralizing antibodies were induced by Asia1-P1Deopt3B3D, mainly at the higher doses.

Figure 23:
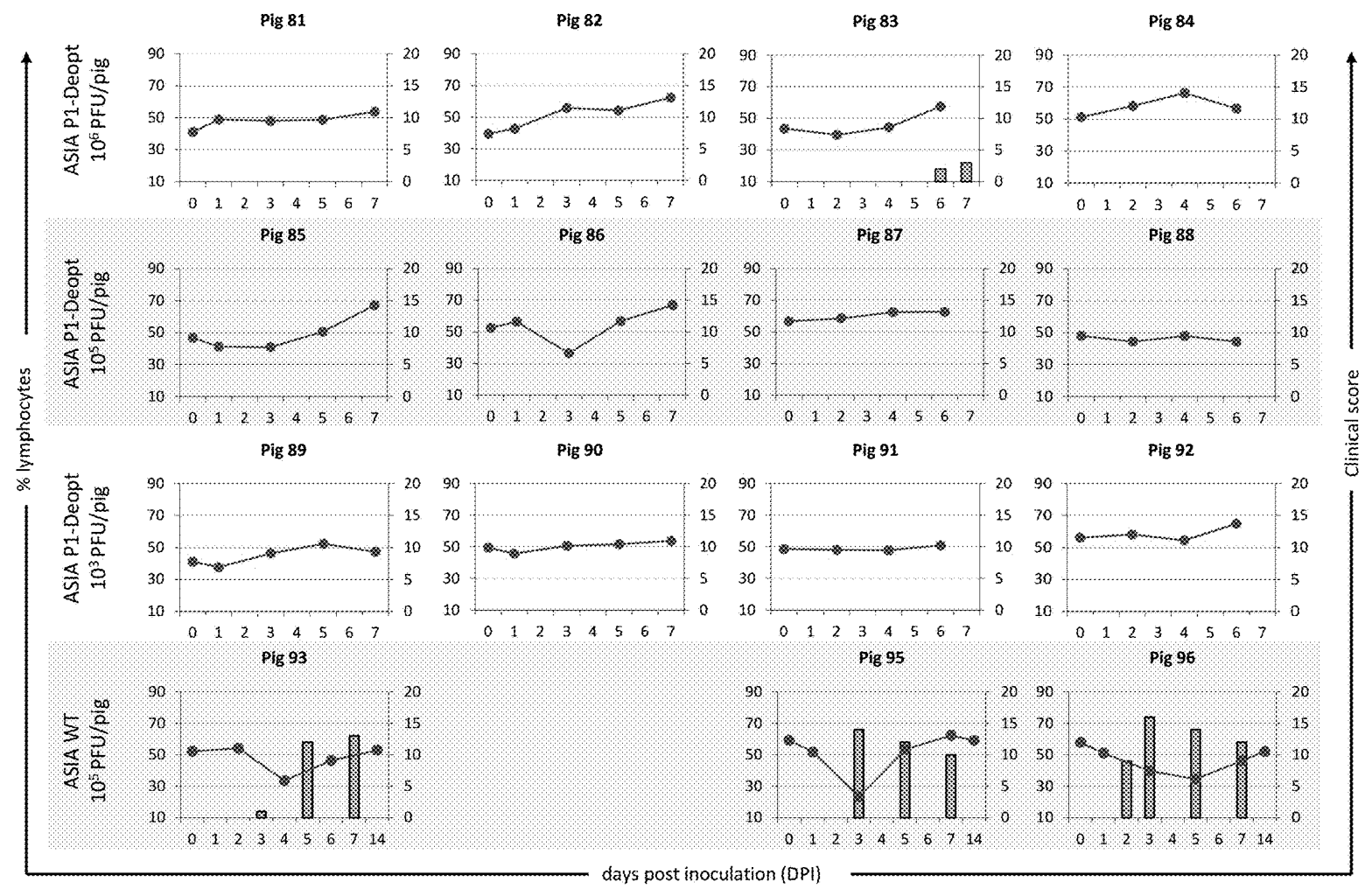
Figure 24:
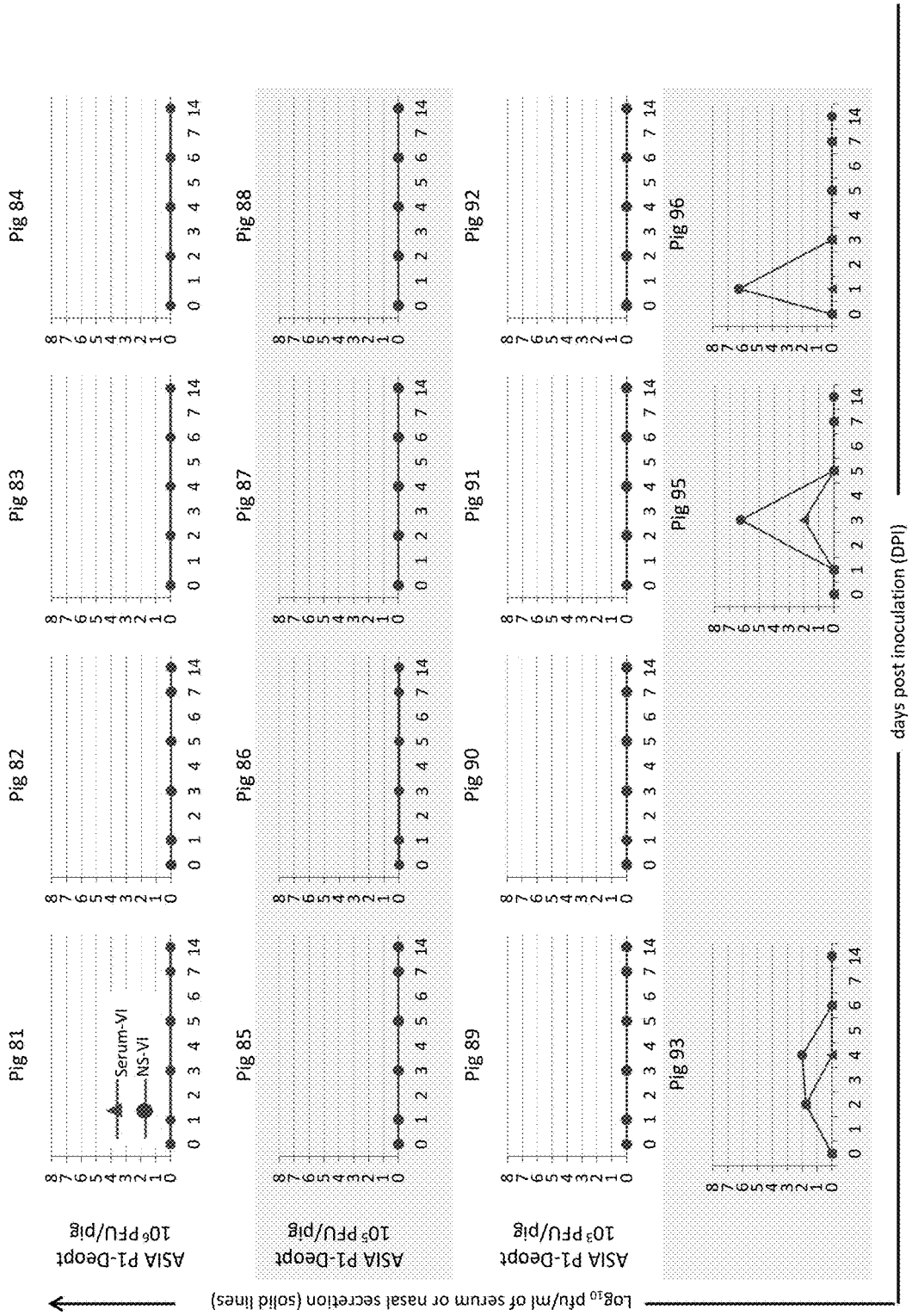
FIG. 24 depicts determination of virus in serum and nasal secretions of animals inoculated with ASIA-P1 Deopt$_{3B3D}$ or ASIA-WT. 18-23 kg castrated male Yorkshire swine (n=4/group) were inoculated with 10$^3$, 10$^5$, or 10$^6$ pfu of FMDV ASIA-P1 Deopt$_{3B3D}$ or 10$^5$ pfu of FMDV ASIA-WT. Animals were monitored for 14 days and samples of serum and nasal swabs were collected daily. The amount of virus was detected by virus isolation in serum (triangle) and nasal secretions (circle).
Figure 25:
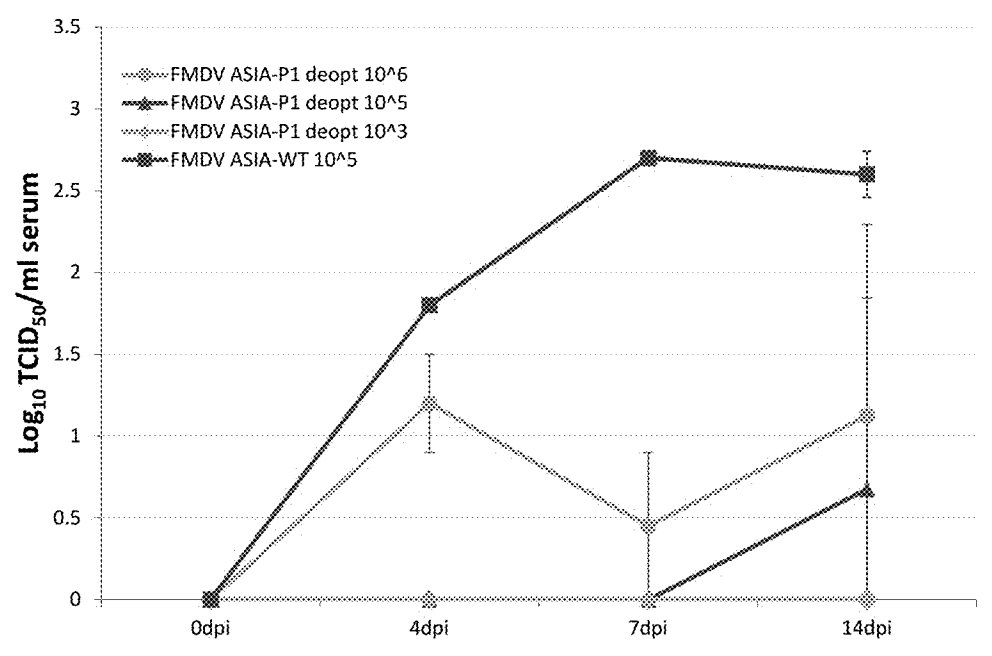

Synonymous Deoptimization of Asia 3B3D P1 Coding Region Results in Attenuation of FMDV in Swine A follow up experiment was performed in swine. Three groups of 4 animals each were inoculated with Asia1P1Deopt3B3D at $10^3$, $10^5$, and $10^6$ pfu/animal, respectively; one group was inoculated with $10^5$ pfu/animal of Asia1 WT as control. Remarkably, eleven out of twelve Asia1P1Deopt3B3D inoculated animals, did not develop clinical signs (FIG. 23). One of the animals inoculated with $10^6$ pfu had a low score (4 out of possible 17) about one-week post inoculation. No viremia or shedding was detected in any of the Asia1P1Deopt3B3D inoculated animals (FIG. 24). In contrast, all animals in the group inoculated with Asia 1 WT virus developed clinical signs including lesions and lymphopenia between 2 and 3 dpi and one animal died by 2 dpi. Consistently, viremia and virus shedding was only detected in animals inoculated with the Asia 1 WT virus. Only animals inoculated with the two highest doses ($10^5$ and $10^6$ pfu/animal) of Asia1P1Deopt$_{3B3D}$ developed a neutralizing antibody response although levels were lower than those elicited by Asia1WT virus. Overall, the antibody titers were lower for Asia1P1Deopt$_{3B3D}$ than those elicited for Asia1P1Deopt$_{3B3D}$ (FIG. 25).

All together these results indicate that deoptimization of the FMDV P1 region causes consistent attenuation independently of the serotype or subtype.

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A deoptimized foot and mouth disease virus (FMDV) comprising a substituted genomic region, wherein the substituted genomic region comprises a nucleic acid at least 95% identical to SEQ ID NO: 1, SEQ ID NO: 2, SEQ ID NO: 3, SEQ ID NO: 4, SEQ ID NO: 5, SEQ ID NO: 6, or SEQ ID NO: 7, and encodes the same polypeptide as SEQ ID NO: 1, SEQ ID NO: 2, SEQ ID NO: 3, SEQ ID NO: 4, SEQ ID NO: 5, SEQ ID NO: 6, or SEQ ID NO: 7, respectively, or encodes the same polypeptide as SEQ ID NO: 1, SEQ ID NO: 2, SEQ ID NO: 3, SEQ ID NO: 4, SEQ ID NO: 5, SEQ ID NO: 6, or SEQ ID NO: 7, respectively, with up to 10 amino acid replacements, deletions or additions.

2. The deoptimized FMDV of claim 1, wherein the substituted genomic region comprises a nucleic acid at least 99% identical to SEQ ID NO: 1.

3. The deoptimized FMDV of claim 2, wherein the substituted genomic region comprises SEQ ID NO: 1.

4. The deoptimized FMDV of claim 1, wherein the substituted genomic region comprises a nucleic acid at least 99% identical to SEQ ID NO: 2.

5. The deoptimized FMDV of claim 4, wherein the substituted genomic region comprises SEQ ID NO: 2.

6. The deoptimized FMDV of claim 1, wherein the substituted genomic region comprises a nucleic acid at least 99% identical to SEQ ID NO: 3.

7. The deoptimized FMDV of claim 6, wherein the substituted genomic region comprises SEQ ID NO: 3.

8. The deoptimized FMDV of claim 1, wherein the substituted genomic region comprises a nucleic acid at least 99% identical to SEQ ID NO: 4.

9. The deoptimized FMDV of claim 8, wherein the substituted genomic region comprises SEQ ID NO: 4.

10. The deoptimized FMDV of claim 1, wherein the substituted genomic region comprises a nucleic acid at least 99% identical to SEQ ID NO: 5.

11. The deoptimized FMDV of claim 10, wherein the substituted genomic region comprises SEQ ID NO: 5.

12. The deoptimized FMDV of claim 1, wherein the substituted genomic region comprises a nucleic acid at least 99% identical to SEQ ID NO: 6.

13. The deoptimized FMDV of claim 12, wherein the substituted genomic region comprises SEQ ID NO: 6.

14. The deoptimized FMDV of claim 1, wherein the substituted genomic region comprises a nucleic acid at least 99% identical to SEQ ID NO: 7.

15. The deoptimized FMDV of claim 14, wherein the substituted genomic region comprises SEQ ID NO: 7.

16. The deoptimized FMDV of claim 1, claim 2, claim 3, claim 4, claim 5, claim 6, claim 7, claim 8, claim 9, claim 10, claim 11, claim 12, claim 13, claim 14, or claim 15, further comprising a DIVA marker.

17. The deoptimized FMDV of claim 16, wherein the DIVA marker comprises mutations in the 3B and 3D coding regions.

18. A deoptimized modified foot and mouth disease virus (FMDV) constructed by substituting the P2 domain, or the P3 domain with a codon deoptimized or codon-pair deoptimized region encoding the same protein sequence, or encoding a protein sequence with up to 10 amino acid replacements, deletions or additions, wherein the codon pair bias of the modified sequence is less than the codon pair bias of the parent FMDV, and is reduced by 0.05, 0.1, or 0.2.

19. The deoptimized modified foot and mouth virus of claim 18, wherein the deoptimized genomic region is the P2 domain.

20. The deoptimized modified foot and mouth virus of claim 18, wherein the deoptimized modified virus is A24-P2-3B3D deoptimized foot and mouth virus.

21. The deoptimized modified foot and mouth virus of claim 18, wherein the deoptimized genomic region is the P3 domain.

22. The deoptimized modified foot and mouth virus of claim 18, wherein the deoptimized modified virus is A24-P3-3B3D deoptimized foot and mouth virus.

23. The deoptimized modified foot and mouth virus of claim 18, wherein the deoptimized genomic region is the P2 domain and the P3 domain.

24. The deoptimized modified foot and mouth virus of claim 18, wherein the deoptimized modified virus is A24-P2/P3-3B3D deoptimized foot and mouth virus.

25. A method of eliciting an immune response to foot and mouth disease, comprising: administering a deoptimized modified virus of claim 1, claim 2, claim 3, claim 4, claim 5, claim 6, claim 7, claim 8, claim 9, claim 10, claim 11, claim 12, claim 13, claim 14, claim 15, claim 18, claim 19, claim 20, claim 21, claim 22, claim 23, or claim 24 to a mammalian subject.

26. The method of claim 25, wherein administering the deoptimized modified virus comprises administering $10^2$, $10^3$, $10^4$ or $10^5$ pfu/mammalian subject of the deoptimized modified virus.

27. The method of claim 26, wherein the subject is a bovid or a suid.

28. The method of claim 25, wherein administering the deoptimized modified virus comprises: administering a prime dose of the deoptimized modified virus to the mammalian subject; and administering one or more boost doses of the deoptimized modified virus to the mammalian subject.

29. The method of claim 28, wherein the prime dose is administered when the mammalian subject does not have foot and mouth disease.

30. The method of claim 28, wherein the one or more boost dose is administered when the mammalian subject does not have foot and mouth disease.

31. The method of claim 28, wherein the one or more boost dose is administered when the mammalian subject has been exposed to foot and mouth disease.

32. The method of claim 25, wherein the immune response is a protective immune response.

* * * * *

SEQUENCE LISTING

<160> NUMBER OF SEQ ID NOS: 7

<210> SEQ ID NO 1
<211> LENGTH: 1517
<212> TYPE: DNA
<213> ORGANISM: Artificial Sequence
<220> FEATURE:
<223> OTHER INFORMATION: Chemically Synthesized

<400> SEQUENCE: 1

```
gctagccggc gacgtcgaat ctaaccccgg tccgtttttt tttagcgacg ttaggtctaa      60
cttttctaag ctcgtcgata ctattaacca aatgcaagaa gatatgagta ctaagcacgg     120
acccgatttt aataggctcg ttagcgcttt cgaagagctc gctaccggcg ttaaggccat     180
taggaccggt ctcgacgaag ctaagccgtg gtataagtta attaaattac ttagccggct     240
tagctgtatg gccgctgtgg cagcacggtc aaaggaccca gtccttgtgg ccatcatgct     300
ggctgacacc ggtctcgaga ttctggacag caccttcgtc gtgaagaaga tctccgactc     360
gctctccagt ctcttccacg tgccggcccc cgtcttcagt ttcggagccc cgattctgtt     420
agccgggttg gtcaaggtcg cctcgagttt cttccggtcc acgcccgaag accttgagag     480
agcagagaaa cagctcaaag cacgtgatat taacgatatc ttcgcaattc ttaagaacgg     540
cgaatggctc gttaagttaa tactcgcaat ccgcgattgg ataaaagcgt ggatcgcaag     600
cgaagaaaaa ttcgttacta ctaccgatct cgtacctagt atcctcgaaa aacaacaaga     660
tcttaacgat cctagtaagt ataaggaagc taaggaatgg ctcgataacg ctaggcaagc     720
gtgtttaaaa tccggtaacg tacatatcgc taacttatgt aaggtcgtcg cacccgctcc     780
tagtaggtct aggcccgagc ccgtcgtcgt atgtttacgc ggtaagtccg gtcaaggtaa     840
gtcgtttctc gctaacgtac tcgcgcaagc gattagtacg cattttaccg gtaggaccga     900
tagcgtatgg tattgtccgc ccgatcccga tcatttcgac ggatataacc aacaaaccgt     960
agtcgttatg gacgatctcg gtcaaaatcc cgacggtaag gattttaaat atttcgcaca    1020
aatggttagc actaccggtt ttatcccgcc tatggctagt ctcgaagata agggtaaacc    1080
gtttaactct aaggttatta tcgctacgac taacttatat agcggtttta cgcctaggac    1140
tatggtatgt cccgacgcac ttaaccgtag gtttcatttc gatatcgacg ttagcgctaa    1200
ggacggatat aagattaaca ataagctcga tatcattaag gcactcgagg atacgcatac    1260
taaccccgtc gctatgtttc aatacgattg cgcattactt aacggtatgg ccgtcgaaat    1320
gaaacgtatg caacaagata tgtttaaacc gcaaccgccg ttacaaaacg tatatcaact    1380
```

| | | |
|---|---|---|
| cgtacaagaa gttatcgaac gcgtcgaatt acacgaaaaa gttagtagcc atcctatctt | 1440 | |
| taagcaaatt agtatcccta gccaaaaaag cgtattatat tttttaatcg aaaaaggtca | 1500 | |
| acacgaagcc gcaattg | 1517 | |

<210> SEQ ID NO 2
<211> LENGTH: 2001
<212> TYPE: DNA
<213> ORGANISM: Artificial Sequence
<220> FEATURE:
<223> OTHER INFORMATION: Chemically Synthesized

<400> SEQUENCE: 2

| | |
|---|---|
| caattgaatt tttcgaaggt atggtacacg atagcattaa ggaagaattg cggccgctaa | 60 |
| tacaacaaac tagcttcgtt aagcgcgcat ttaagcgact taaggaaaat ttcgaaatcg | 120 |
| tcgcgttatg tcttacgtta ctcgctaata tcgttattat gatacgcgaa actcgtaagc | 180 |
| gacaaaaaat ggtcgatgac gccgttagcg aatatatcga acgcgctaac attacgaccg | 240 |
| acgataagac gctcgacgaa gccgaaaaaa atccgctcga aactagcggc gctagtaccg | 300 |
| tcggattccg cgaacgaccg ttacccggtc aaaaagctag gaacgacgaa aactccgaac | 360 |
| ccgctcagcc tgcagaagag caaccacaag ctgaaggacc ctacgctggc ccgatggaga | 420 |
| gaccagttaa agttaaagtg aaagcaaaag ccccggtcgt taaggaagga ccttacgagg | 480 |
| gaccggtgaa gaagcctgtt gctttgaaag tgaaagctaa gaacttgatc gtcactgaga | 540 |
| gtggtgcccc accgaccgac ttgcaaaagt tggtcatggg caacaccaag cccgttgagc | 600 |
| tcatccttga cgggaagacg gtagccattt gctgtgctac tggagttttc ggcactgctt | 660 |
| acctcgtgcc tcgtcatctt ttcgcagaaa agtacgacaa gatcatgttg gacggcagag | 720 |
| ccatgacaga tagtgactac agagtgtttg agtttgagat taaagtaaaa ggacaggaca | 780 |
| tgctctcaga cgctgcgctc atggtgctcc accgtgggaa tcgcgtgaga gacatcacga | 840 |
| aacactttcg tgacacagca agaatgaaga aaggcacccc cgtcgttggt gtgatcaaca | 900 |
| acgccgatgt cgggagactg attttctctg gtgaagcgtt aacgtataag gatatcgtcg | 960 |
| tatgtatgga cggcgatact atgcccggtt tattcgcata taaggccgct actaaggccg | 1020 |
| gatattgcgg aggcgccgta ctcgctaagg acggagccga tacgtttatc gtaggtacgc | 1080 |
| atagcgccgc cggtaacggc gtcggatatt gtagctgcgt tagccgtagt atgcttctta | 1140 |
| agatgaaagc gcacgtcgat cccgaaccgc atcacgaagg tttaatcgtc gatacccgcg | 1200 |
| acgtcgaaga acgcgtacac gttatgcgta agactaagct cgcacctacc gtcgcatacg | 1260 |
| gcgtatttag gcccgaattc ggacccgccg cacttagcaa taaagatcct aggcttaacg | 1320 |
| acggcgtcgt actcgacgaa gttatcttta gtaagcataa gggcgatact aagatgtccg | 1380 |
| aagaagataa ggcgttattc cgtaggtgcg ccgccgatta cgctagtagg ttacatagcg | 1440 |
| tactcggtac cgctaacgct ccgcttagta tctacgaagc gattaagggc gtagacggac | 1500 |
| tcgacgctat ggaacccgat accgctcccg gtttaccgtg ggcgttacaa ggtaagcgta | 1560 |
| ggggcgcatt aatcgatttc gaaaacggta ccgtcggacc cgaagtcgaa gccgcactta | 1620 |
| agcttatgga aaaacgcgaa tataagttcg catgtcaaac gtttcttaag gacgaaatta | 1680 |
| ggcctatgga aaaagttagg gccggtaaga ctaggattgt cgacgtatta cccgtcgaac | 1740 |
| atatattata tactaggatg atgatcggta ggttttgcgc gcaaatgcat agtaataacg | 1800 |
| gtccgcaaat cggtagcgcc gtcggatgta acccgacgt cgattggcaa cgattcggta | 1860 |

| | |
|---|---|
| cgcatttcgc acaatatcgt aacgtatggg acgtcgatta tagcgctttc gacgctaacc | 1920 |
| attgtagcga cgctatgaat ataatgttcg aagaagtatt taggaccgaa ttcggttttc | 1980 |
| atcctaacgc cgaatggatc c | 2001 |

<210> SEQ ID NO 3
<211> LENGTH: 3512
<212> TYPE: DNA
<213> ORGANISM: Artificial Sequence
<220> FEATURE:
<223> OTHER INFORMATION: Chemically Synthesized

<400> SEQUENCE: 3

| | |
|---|---|
| gctagccggc gacgtcgaat ctaaccccgg tccgtttttt tttagcgacg ttaggtctaa | 60 |
| cttttctaag ctcgtcgata ctattaacca aatgcaagaa gatatgagta ctaagcacgg | 120 |
| acccgatttt aataggctcg ttagcgcttt cgaagagctc gctaccggcg ttaaggccat | 180 |
| taggaccggt ctcgacgaag ctaagccgtg gtataagtta attaaattac ttagccggct | 240 |
| tagctgtatg gccgctgtgg cagcacggtc aaaggaccca gtccttgtgg ccatcatgct | 300 |
| ggctgacacc ggtctcgaga ttctggacag caccttcgtc gtgaagaaga tctccgactc | 360 |
| gctctccagt ctcttccacg tgccggcccc cgtcttcagt ttcggagccc cgattctgtt | 420 |
| agccgggttg gtcaaggtcg cctcgagttt cttccggtcc acgcccgaag accttgagag | 480 |
| agcagagaaa cagctcaaag cacgtgatat taacgatatc ttcgcaattc ttaagaacgg | 540 |
| cgaatggctc gttaagttaa tactcgcaat ccgcgattgg ataaaagcgt ggatcgcaag | 600 |
| cgaagaaaaa ttcgttacta ctaccgatct cgtacctagt atcctcgaaa acaacaaga | 660 |
| tcttaacgat cctagtaagt ataaggaagc taaggaatgg ctcgataacg ctaggcaagc | 720 |
| gtgtttaaaa tccggtaacg tacatatcgc taacttatgt aaggtcgtcg cacccgctcc | 780 |
| tagtaggtct aggcccgagc ccgtcgtcgt atgtttacgc ggtaagtccg gtcaaggtaa | 840 |
| gtcgtttctc gctaacgtac tcgcgcaagc gattagtacg catttaccg gtaggaccga | 900 |
| tagcgtatgg tattgtccgc ccgatcccga tcatttcgac ggatataacc aacaaaccgt | 960 |
| agtcgttatg gacgatctcg gtcaaaatcc cgacggtaag gatttaaat atttcgcaca | 1020 |
| aatggttagc actaccggtt ttatcccgcc tatggctagt ctcgaagata agggtaaacc | 1080 |
| gtttaactct aaggttatta tcgctacgac taacttatat agcggtttta cgcctaggac | 1140 |
| tatggtatgt cccgacgcac ttaaccgtag gtttcatttc gatatcgacg ttagcgctaa | 1200 |
| ggacggatat aagattaaca ataagctcga tatcattaag gcactcgagg atacgcatac | 1260 |
| taaccccgtc gctatgtttc aatacgattg cgcattactt aacggtatgg ccgtcgaaat | 1320 |
| gaaacgtatg caacaagata tgtttaaacc gcaaccgccg ttacaaaacg tatatcaact | 1380 |
| cgtacaagaa gttatcgaac gcgtcgaatt acacgaaaaa gttagtagcc atcctatctt | 1440 |
| taagcaaatt agtatcccta gccaaaaaag cgtattatat ttttaatcg aaaaaggtca | 1500 |
| acacgaagcc gcaattgaat ttttcgaagg tatggtacac gatagcatta aggagaatt | 1560 |
| gcggccgcta atacaacaaa ctagcttcgt taagcgcgca tttaagcgac ttaaggaaaa | 1620 |
| tttcgaaatc gtcgcgttat gtcttacgtt actcgctaat atcgttatta tgatacgcga | 1680 |
| aactcgtaag cgacaaaaaa tggtcgatga cgccgttagc gaatatatcg aacgcgctaa | 1740 |
| cattacgacc gacgataaga cgctcgacga agccgaaaaa aatccgctcg aaactagcgg | 1800 |
| cgctagtacc gtcggattcc gcgaacgacc gttacccggt caaaaagcta ggaacgacga | 1860 |
| aaactccgaa cccgctcagc ctgcagaaga gcaaccacaa gctgaaggac cctacgctgg | 1920 |

```
cccgatggag agaccagtta aagttaaagt gaaagcaaaa gccccggtcg ttaaggaagg      1980
accttacgag ggaccggtga agaagcctgt tgctttgaaa gtgaaagcta agaacttgat      2040
cgtcactgag agtggtgccc caccgaccga cttgcaaaag ttggtcatgg caacaccaa       2100 gcccgttgag ctcatccttg acgggaagac ggtagccatt tgctgtgcta ctggagtttt      2160
cggcactgct tacctcgtgc ctcgtcatct tttcgcagaa aagtacgaca agatcatgtt      2220
ggacggcaga gccatgacag atagtgacta cagagtgttt gagtttgaga ttaaagtaaa      2280
aggacaggac atgctctcag acgctgcgct catggtgctc caccgtggga atcgcgtgag      2340
agacatcacg aaacactttc gtgacacagc aagaatgaag aaaggcaccc cgtcgttgg       2400 tgtgatcaac aacgccgatg tcgggagact gattttctct ggtgaagcgt taacgtataa      2460
ggatatcgtc gtatgtatgg acggcgatac tatgcccggt ttattcgcat ataaggccgc      2520
tactaaggcc ggatattgcg gaggcgccgt actcgctaag gacggagccg atacgtttat      2580
cgtaggtacg catagcgccg gcggtaacgg cgtcggatat tgtagctgcg ttagccgtag      2640
tatgcttctt aagatgaaag cgcacgtcga tcccgaaccg catcacgaag gtttaatcgt      2700
cgatacccgc gacgtcgaag aacgcgtaca cgttatgcgt aagactaagc tcgcacctac      2760
cgtcgcatac ggcgtattta ggcccgaatt cggacccgcc gcacttagca ataaagatcc      2820
taggcttaac gacggcgtcg tactcgacga agttatcttt agtaagcata agggcgatac      2880
taagatgtcc gaagaagata aggcgttatt ccgtaggtgc gccgccgatt acgctagtag      2940
gttacatagc gtactcggta ccgctaacgc tccgcttagt atctacgaag cgattaaggg      3000
cgtagacgga ctcgacgcta tggaacccga taccgctccc ggtttaccgt gggcgttaca      3060
aggtaagcgt aggggcgcat taatcgattt cgaaaacggt accgtcggac ccgaagtcga      3120
agccgcactt aagcttatgg aaaaacgcga atataagttc gcatgtcaaa cgtttcttaa      3180
ggacgaaatt aggcctatgg aaaaagttag ggccggtaag actaggattg tcgacgtatt      3240
acccgtcgaa catatattat atactaggat gatgatcggt aggttttgcg cgcaaatgca      3300
tagtaataac ggtccgcaaa tcggtagcgc cgtcggatgt aaccccgacg tcgattggca      3360
acgattcggt acgcatttcg cacaatatcg taacgtatgg gacgtcgatt atagcgcttt      3420
cgacgctaac cattgtagcg acgctatgaa tataatgttc gaagaagtat ttaggaccga      3480
attcggtttt catcctaacg ccgaatggat cc                                    3512

<210> SEQ ID NO 4
<211> LENGTH: 2234
<212> TYPE: DNA
<213> ORGANISM: Artificial Sequence
<220> FEATURE:
<223> OTHER INFORMATION: Chemically Synthesized

<400> SEQUENCE: 4
ggggccggcc aatcgagtcc cgctaccggt tcgcaaaacc aatccggtaa caccggatcg        60
atcattaaca attactatat gcagcaatac cagaactcta tggacacaca gttgggcgac       120
aacgctatct ccggcggatc gaacgagggg tcaaccgaca ctacgagtac gcatacgact       180
aacacacaga ataacgattg ttttcgaag ctcgcttcat ccgcttttac cgggttgttc        240
ggcgcactgc ttgccgataa gaagaccgaa gagactacgt tgctcgagga ccggattctg       300
actacgcgta acgtcacaca acatcgacaa acgcaatcgt cagtcggcgt gacacacggg       360
tactcaaccg aagaggacca cgtcgccgga ccgaacacta gcggactcga gacacgcgtt       420
```

-continued

```
gtgcaggccg aacggtttta caaaaagtat ctgttcgatt ggactaccga caaagcgttc        480
ggtcacctcg agaaactcga gttgcctagc gaccaccacg gcgtgttcgg gcaccttgtc        540
gactcatacg cttacatgcg taacgggtgg gacgtcgagg tgtccgccgt aggcaatcag        600
ttcaacgggg ggtgcctgtt ggtcgcgatg gtgcccgaat ggaaagagtt cgacacacgc        660
gaaaagtacc aactgacact gttccgcac caattcatta gtccgcgaac gaacatgacc         720
gctcacatta ccgtgccata ccttggcgtt aacagatacg accaatacaa aaagcacaag        780
ccttggacac tcgttgtgat ggtcgtgagt ccgcttaccg ttaacaacac tagtgccgca        840
cagattaagg tgtacgctaa catcgcaccg acatacgtgc acgtcgccgg cgaattgccg        900
tctaaggagg ggatctttcc cgtcgcatgc gccgacggat acggcggact cgtgactacc        960 gacccctaaga ccgccgaccc cgcatacggt aaggtgtaca atccgcctag aactaactac       1020
cccggtaggt ttacgaactt gctcgacgtc gccgaagcgt gtccgacatt cttgtgcttc       1080
gacgacggta agccatacgt tacgacacga accgacgaca ctagactgct tgcgaaattc       1140
gacctgtcac tcgccgctaa gcatatgtct aacacatacc tatccggtat cgcgcaatac       1200
tatacgcaat actccggtac gattaacttg cactttatgt ttaccggatc gaccgactct       1260
aaggctaggt atatggtcgc atacattccg cctggcgtcg agacaccccc cgacacaccc       1320
gaacgcgccg cacactgtat ccacgccgaa tgggacaccg gcttaactc taagtttacg         1380 ttttcgatcc catacgtgtc cgccgcggat tacgcataca ccgcgagcga taccgccgaa        1440
acgattaacg tgcaggggtg ggtgtgcata taccagatta cgcacggtaa ggccgaaaac       1500
gacacactcg tagtgtccgt tagcgccggt aaggacttcg agttgcggtt gccgatcgac       1560
cctagacagc agactaccgc taccggcgaa tccgccgacc cagtgactac gacagtcgag       1620
aattacggcg gtgagacaca gatccaacgg agacaccata ccgacatagg gttcattatg       1680
gacagattcg ttaagataca gtcactgtca ccgacacacg tgatcgacct tatgcagaca       1740
caccaacacg gactcgtagg cgcactgttg cgcgccgcta catactactt ttccgaccctc      1800 gagatcgtcg tgcgacacga gggtaacctg acatgggtgc ctaacggcgc acccgaatcc       1860
gcactgctta acactagcaa tccgaccgca tacaacaaag cgccattcac acgactcgca       1920
ctgccataca ccgcaccgca tagggtgctt gcgacagtgt acaacggtac gtctaagtac       1980
gccgtaggcg ggtccggtag acgcggcgac atggggtcac tcgccgctag ggtggttaag       2040
cagttgcccg ccagctttaa ctacggcgca atcaaggccg acgctatcca cgaactgctt       2100
gtgcgtatga aacgcgccga actgtattgc cctagaccgt tgctcgcgat cgaggtgagt       2160
tcgcaagaca gacacaaaca gaagattatc gccccgcta agcagcttct gaattttgac        2220
ctgctcaagc tagc                                                          2234
```

<210> SEQ ID NO 5
<211> LENGTH: 2222
<212> TYPE: DNA
<213> ORGANISM: Artificial Sequence
<220> FEATURE:
<223> OTHER INFORMATION: Chemically Synthesized

<400> SEQUENCE: 5

```
ggggccggcc aatctagtcc cgctaccggt agtcagaacc agtccggtaa caccggatcg         60
atcattaaca actactatat gcagcaatac cagaactcta tggacacaca gttgggcgat        120
aacgctatct caggcggatc gaacgagggg tcgaccgaca ctacctctac gcacactaac        180
aacacacaga ataacgactg gttttcgcga cttgcttcta gcgcgtttag cggactgttc        240
```

```
ggcgcactgc ttgccgataa gaagaccgaa gagactacgt tgctcgagga tcgcatactg    300
actacgcgta acggtcacac tacgagtacg acacagtcta gcgtaggcgt gacatacgga    360
tacgccgttg cggaggacgc cgttagcgga ccgaacacta gcggactcga gacacgcgta    420
cagcaggccg aacggttctt taagaaacac ctattcgatt ggactccgaa cctcgcattc    480
ggacactgtt actatctcga gttgccgacc gaacacaaag gcgtgtacgg atcgcttatg    540
gggtcatacg catacatgcg taacgggtgg gacatcgagg tgaccgcagt cggtaaccag    600
tttaacgggg ggtgtctgtt agtcgcgctt gtgcccgaac tgaaagagct tgacacacgc    660
caaaagtacc aactgacact gttcccacac caattcatta accctaggac taacatgacc    720
gctcacatta acgtgccata cgtcggtatc aatcggtacg accaatacgc tctgcacaag    780
ccttggacac tcgtcgtgat ggtcgtcgca ccccttaccg ttaagaccgg cgggtccgaa    840
cagattaagg tgtatatgaa cgctgcgcca acatacgtgc acgttgccgg cgagttgccg    900
tctaaggagg ggatcgtgcc cgtcgcatgc gccgacggat acggtaacat ggtgactacc    960
gaccctaaga ccgccgaccc cgtgtacggt aaggtgttca accccccccg cactaacctg   1020
cccggtaggt ttacgaactt tctcgacgtc gccgaagcgt gccctacatt ccttaggttc   1080
ggcgaagtgc cattcgttaa gaccgtgaac tccggcgatc gcttgctcgc gaaattcgac   1140
gtgtcactcg ccgccggtca catgtctaac acataccttg ccggactcgc gcaatactat   1200
acgcaatact ccggtacgat gaacgtgcac tttatgttta ccggaccgac cgacgctaag   1260
gctaggtata tggtcgcgta cgttccccccc ggtatgacac cccctaccga ccccgaacac   1320
gccgcacact gtatccactc tgagtgggac accggactta actctaagtt tacgttttcg   1380
atcccatacc tatccgccgc ggactacgct tacaccgcga gcgacgttgc cgaaacgact   1440
agcgtgcagg ggtgggtgtg tatctaccag attacgcacg gtaaggccga aggcgacgca   1500
ctcgtcgtga gtgtgtccgc cggtaaggac ttcgagtttc gcttgcccgt tgacgctagg   1560
cagcagacta cgactaccgg cgaatccgcc gatcccgtta cgactaccgt cgagaactac   1620
ggcggagaga cacagaccgc taggcgactg cataccgacg ttgcgttcat actcgaccgg   1680
ttcgttaagc ttaccgcgcc taagaatatc cagacactcg accttatgca gatcccgtca   1740
cacacactcg taggcgcact gttgcgctct gcgacatact acttttccga cctcgaggtc   1800
gcgcttgtgc acaccggtcc cgtgacatgg gtgcctaacg gcgcaccgaa agacgcactg   1860
aacaaccaga ctaaccctac cgcataccag aaacgcccta ttacgcgact cgcactgcca   1920
tacaccgcac cccatagggt gcttgcgacc gtgtataacg gtaagaccgc atacggcgag   1980
actacctcta ggcgcggcga catggccgca ctcgcgcaac gcctatccgc tagactgcca   2040
acgtcattca attacggcgc cgttaaggcc gatacgatca ccggactgct tatccgtatg   2100
aaacgcgctg agacatactg tccacgcccc ctactcgcac tcgatacgac tcaggacaga   2160
cgcaaacagg agataatcgc acccgagaaa cagcttctga tttttgacct gcttaagcta   2220
gc                                                                  2222
```

<210> SEQ ID NO 6
<211> LENGTH: 2231
<212> TYPE: DNA
<213> ORGANISM: Artificial Sequence
<220> FEATURE:
<223> OTHER INFORMATION: Chemically Synthesized

<400> SEQUENCE: 6

```
ggggccggcc aatcgagtcc cgctactggg tcacagaacc agtccggtaa taccggatcg        60
atcattaaca actactatat gcagcaatac cagaattcaa tggacacaca gttaggcgat       120
aacgctacta gcgggggggtc gaacgagggg tcaaccgata cgaccagtac gcacactacg       180
aacacacaga acaatgattg gttttcgaaa ctcgctagtt ccgcttttag cggactgttc       240
ggcgctctgc ttgcggacaa aaagaccgaa gagactacac tgcttgagga ccgcatactg       300
actacccgta acgggcatac gactagcact acccagtcta gcgtaggcgt gacatacggg       360
tacgctaccg ccgaagactt cgttagcgga ccgaacacta gcggactcga gacacgcgtt       420
gcgcaagccg aacggttctt taagacacac ctgttcgatt gggtgactag cgacccattc       480
ggtaggtgcc acttgctcga gttgcctacc gaccacaaag gggtgtacgg atcgcttacc       540
gactcatacg cttacatgcg taacgggtgg gacgtcgagg tgaccgcagt cggtaaccaa       600
ttcaacgggg ggtgcttgct cgttgcgatg gtgcctgagt tgtgctcaat ccagaaacgc       660
gaactgtatc agcttacact gtttccgcac caattcatta accctaggac taacatgacc       720
gctcacatta ccgtgccatt cgtaggcgtg aaccggtacg accaatacaa agtgcacaaa       780
ccttggacac tggtcgtgat ggtggtcgca ccgcttaccg ttaattccga gggagcgcca       840
cagattaagg tgtacgctaa catcgcaccg actaacgtgc acgtcgccgg tgagttccct       900
agcaaagagg gtatctttcc ggtcgcatgc tccgacggat acgggggggtt agtgactacc       960
gacccctaaga ccgctgaccc tgcgtacggt aaggtgttca acccgccacg taatatgttg      1020
cccggtcggt ttacgaactt tctcgacgtc gccgaggcat gccctacatt cttgcacttc      1080
gagggcgacg tgccatacgt tacgactaag accgactccg ataggggtgct tgcgcaattc      1140
gacctgtcac tcgccgctaa gcacatgtcg aacacattcc ttgccggact cgcgcaatac      1200
tatacgcaat actccggtac gatcaacctg cactttatgt ttaccggacc taccgacgct      1260
aaggctaggt atatgatcgc atacgctccc cccggtatgg agcctcctaa gactcccgaa      1320
gccgccgctc actgtatcca cgccgaatgg gacaccggac tgaattctaa gtttacgttc      1380
tcaatcccat acctatccgc cgctgactac gcttacaccg cgagcgatac cgctgagact      1440
acgaacgtgc aggggtgggt gtgcctgttt cagattacgc acggtaaggc cgacggcgac      1500
gcactcgtag tgctcgcaag cgccggtaag gacttcgagc ttagactgcc agtcgacgct      1560
aggacacaga ctacctccgc gggcgaatcc gccgacccag tgaccgctac cgtcgagaac      1620
tacggcggag agacacaggt gcagcgtaga cagcacaccg acgtgtcatt catactcgac      1680
agattcgtta aggtgacacc gaaagaccag attaatgtgc ttgacccttat gcagacaccc      1740
gctcacacac tcgtaggcgc actgttgcga accgctacct attacttcgc tgaccttgag      1800
gtcgccgtta agcacgaggg taacctgaca tgggtgccta acggcgcacc cgaagccgca      1860
ctcgacaaca cgactaatcc taccgcatac cacaaagcgc cactgacacg gcttgcgttg      1920
ccgtataccg ctccacaccg cgtactcgct accgtgtata acggtaactc taagtacggc      1980
gacggtaccg ttgcgaacgt tagggggcgac ttgcaggtgc ttgcgcaaaa ggccgcacgc      2040
gcactgccta ctagctttaa ctacggtgcg atcaaagcga cacgcgttac cgagttgctg      2100
tatcggatga aacgcgctga gacatattgc cctagaccgt tgctcgcgat acaccctgac      2160
caggctaggc acaaacagaa aatcgtcgca cccgtgaaac agctgcttaa cttcgacctg      2220
ttgaagctag c                                                          2231
```

<210> SEQ ID NO 7
<211> LENGTH: 2231

```
<212> TYPE: DNA
<213> ORGANISM: Artificial Sequence
<220> FEATURE:
<223> OTHER INFORMATION: Chemically Synthesized

<400> SEQUENCE: 7
```

| | | | | |
|---|---|---|---|---|
| ggggccggcc | aatctagtcc | cgctaccggt | agtcagaacc | agtccggtaa | caccggatcg | 60 |
| atcattaaca | attactacat | gcagcaatat | cagaactcta | tggacacaca | gttgggcgac | 120 |
| aacgctatct | ccggcggatc | gaacgagggg | tctaccgaca | ctacctctac | ccatacgact | 180 |
| aacacacaga | acaacgattg | gttttcgaaa | ctcgcttcta | gcgcttttag | cggactgttc | 240 |
| ggcgcactgc | ttgcggacaa | aaagaccgag | gagactaccc | ttctcgaaga | ccgcatactg | 300 |
| acaacccgta | acggtcacac | taccagtacg | acacagtcta | gcgttggcgt | gacatacggg | 360 |
| tacgctaccg | ccgaagactt | cgttagcgga | ccgaacacta | gcggactcga | gacacgcgta | 420 |
| gtgcaggccg | aacggttctt | taagacacac | ttgttcgatt | gggtgacatc | cgactcattc | 480 |
| ggtaggtgcc | acctactcga | gttgccgacc | gaccacaagg | gcgtgtacgg | atcgcttacc | 540 |
| gactcatacg | catacatgcg | taacgggtgg | gacgtcgagg | tgaccgcagt | cggtaaccag | 600 |
| tttaacggcg | gatgcctgtt | ggtcgcgatg | gtgccagagt | tgcggtctat | ccagaaacgc | 660 |
| gaactgtacc | aactgacact | gttcccacac | caattcatta | acccacgcac | taacatgacc | 720 |
| gcacacatta | ccgtgccatt | cgtcggcgtt | aaccggtatg | accagtacaa | agtgcacaaa | 780 |
| ccgtggacac | tcgtagtgat | ggtcgttgcg | ccacttaccg | taaacaccga | gggcgcacca | 840 |
| cagattaagg | tgtacgctaa | cattgcgcct | actaacgtgc | acgtcgccgg | cgaattccct | 900 |
| agtaaggagg | ggatctttcc | cgtcgcatgc | tccgacggat | acggcggact | cgtgactacc | 960 |
| gatccgaaaa | ccgccgaccc | cgtgtacggt | aaggtgttta | acccaccgcg | taaccagttg | 1020 |
| cccggtcggt | ttacgaacct | tctcgacgtc | gccgaagcgt | gccctacatt | cttgcacttc | 1080 |
| gagggcgacg | tgccatacgt | tacgactaag | accgactccg | atagggtgct | tgcgcaattc | 1140 |
| gacatgagtc | tcgctgcgaa | acacatgtct | aacacattcc | ttgccggact | cgcgcaatac | 1200 |
| tacacgcaat | attccggtac | gatcaatctg | cactttatgt | ttaccggtcc | gaccgacgct | 1260 |
| aaggctaggt | acatgatcgc | atatgctccc | cccggtatgg | aaccccctaa | gaccccgaa | 1320 |
| gcggccgcac | actgcataca | cgccgaatgg | gacaccggac | tgaactctaa | gtttacgttt | 1380 |
| tcgatcccat | acctatccgc | ggccgactac | gcatacaccg | cgagcgacgt | cgccgaaacc | 1440 |
| actaacgtgc | agggggtgggt | gtgtctgttc | cagattaccc | acggtaaggc | cgacggcgac | 1500 |
| gcactcgtag | tgctcgcgag | cgccggtaag | gacttcgagt | tgcggttgcc | cgtcgacgct | 1560 |
| agggccgaga | ctacctccgc | cggtgagtcc | gccgatcccg | ttaccgctac | cgtcgagaac | 1620 |
| tacggcggtg | agacacagat | tcagcgtaga | cagcacaccg | acgtgtcatt | cattatggac | 1680 |
| agattcgtta | aggtgacacc | gcaaaaccag | attaacatac | tcgacctat | gcagattccg | 1740 |
| tcacacacac | tcgtaggcgc | actgttgcgc | gcgagcacat | actactttc | cgacctcgag | 1800 |
| atcgccgtta | agcacgaggg | cgatctgaca | tgggtgccta | acggcgcacc | cgagaaagcg | 1860 |
| cttgacaata | cgactaaccc | taccgcatac | cacaaagcgc | cactgactag | actcgcgctt | 1920 |
| ccgtacaccg | caccgcatag | ggtgcttgcg | accgtgtata | acggcgagtg | taggtactca | 1980 |
| cgtaacgccg | ttccgaacgt | gagaggcgac | cttcaggtgc | ttgcgcaaaa | ggtcgcgaga | 2040 |
| accctgccta | cctcattcaa | ttacggcgca | atcaaagcga | cacgcgttac | cgaactgttg | 2100 |

```
taccgtatga aacgcgccga aacctactgc cctagaccgt tgctcgcgat ccaccctatc    2160
gaggctaggc acaaacagaa aatcgtcgca cccgttaagc agcttctgaa ttttgacctg    2220
cttaagctag c                                                        2231
```